US010052060B2

(12) United States Patent
Lytle et al.

(10) Patent No.: US 10,052,060 B2
(45) Date of Patent: *Aug. 21, 2018

(54) SYSTEM AND METHOD FOR ADJUSTING ALIGNMENT OF A BODY PART WITH AN IMAGING APPARATUS

(71) Applicants: Andrew B. Lytle, Farmington Hills, MI (US); James J. Verner, Beverly Hills, MI (US)

(72) Inventors: Andrew B. Lytle, Farmington Hills, MI (US); James J. Verner, Beverly Hills, MI (US)

( * ) Notice: Subject to any disclaimer, the term of this patent is extended or adjusted under 35 U.S.C. 154(b) by 690 days.

This patent is subject to a terminal disclaimer.

(21) Appl. No.: 14/530,386

(22) Filed: Oct. 31, 2014

(65) Prior Publication Data

US 2015/0117608 A1    Apr. 30, 2015

Related U.S. Application Data

(60) Provisional application No. 61/898,228, filed on Oct. 31, 2013.

(51) Int. Cl.
*A61B 5/00* (2006.01)
*A61B 6/04* (2006.01)
(Continued)

(52) U.S. Cl.
CPC ............ *A61B 5/4571* (2013.01); *A61B 6/463* (2013.01); *G06T 7/0014* (2013.01); *G06T 7/33* (2017.01);
(Continued)

(58) Field of Classification Search
CPC .. A61B 6/00; A61B 6/03; A61B 6/032; A61B 6/04; A61B 6/0457; A61B 6/0492; A61B 6/46; A61B 6/461; A61B 6/463; A61B 6/465–6/467; A61B 6/469; A61B 6/50; A61B 6/505; A61B 6/52; A61B 6/5211; A61B 6/5217; A61B 6/5223; A61B 6/5229; A61B 6/5235; A61B 6/54; A61B 6/542; A61B 6/544; A61B 6/545;
(Continued)

(56) References Cited

U.S. PATENT DOCUMENTS 8,611,504 B2 * 12/2013 Kubiak ................. A61B 19/26
33/512
8,644,909 B2 * 2/2014 Cooke ...................... G06G 7/60
600/407

(Continued)

*Primary Examiner* — Anastasia Midkiff
(74) *Attorney, Agent, or Firm* — Honigman Miller Schwartz and Cohn LLP

(57) ABSTRACT

A method includes a obtaining an image of a center of a pelvis of a patient captured by an imaging device and analyzing the image of the pelvis center to determine whether or not the pelvis center is aligned with the imaging device using a computing device. When the pelvis center is not aligned with the imaging device, the method includes determining one or more alignment instructions for aligning the pelvis center with the imaging device by the computing device and transmitting the analyzed image of the pelvis center and the one or more pelvis alignment instructions to a user device in communication with the computing device. The user device executes a graphical user interface for displaying the analyzed image and one or more pelvis alignment instructions.

30 Claims, 19 Drawing Sheets

(51) Int. Cl.
 *A61B 17/17*  (2006.01)
 *G06T 7/33*  (2017.01)
 *G06T 7/73*  (2017.01)
 *G06T 7/00*  (2017.01)
 *A61B 6/00*  (2006.01)
 *A61B 34/10*  (2016.01)

(52) U.S. Cl.
 CPC .............. *G06T 7/73* (2017.01); *A61B 6/0407* (2013.01); *A61B 6/0457* (2013.01); *A61B 6/0492* (2013.01); *A61B 6/4405* (2013.01); *A61B 6/4441* (2013.01); *A61B 6/469* (2013.01); *A61B 6/544* (2013.01); *A61B 17/1703* (2013.01); *A61B 17/1742* (2013.01); *A61B 34/10* (2016.02); *A61B 2034/107* (2016.02); *A61B 2034/108* (2016.02); *G06T 2207/20044* (2013.01); *G06T 2207/20068* (2013.01); *G06T 2207/30008* (2013.01); *G06T 2207/30052* (2013.01)

(58) Field of Classification Search
 CPC ........... A61B 6/58; A61B 6/585; A61B 6/589; A61B 2560/00; A61B 2560/02; A61B 2560/0223; A61B 2576/00; A61B 2576/02; A61B 5/00; A61B 5/45; A61B 5/4504; A61B 5/4538; A61B 5/4571; A61B 17/17; A61B 17/1703; A61B 17/1739; A61B 17/1742; A61B 17/175; A61B 17/1753; G01N 23/00; G01N 23/02; G01N 23/04; G01N 23/046; G01N 23/06; G01N 23/08; G01N 23/083; G01N 2223/40; G01N 2223/402; G01N 2223/403; G01N 2223/41; G01N 2223/417; G01N 2223/419; G01N 2223/42; G01N 2223/422; G01N 2223/60; G01N 2223/612; G06T 7/0012; G06T 7/0014; G06T 7/0016; G06T 7/174; G06T 7/30; G06T 7/33; G06T 7/344; G06T 7/60; G06T 7/68; G06T 7/70; G06T 7/73; G06T 7/75; G06T 7/97; G06T 19/00003; G06T 2219/00; G06T 2219/004; G06T 2219/008; G06T 2219/20; G06T 2219/2012; G06T 2219/2016; G06T 2207/00; G06T 2207/10; G06T 2207/10072; G06T 2207/10081; G06T 2207/20; G06T 2207/20036; G06T 2207/20044; G06T 2207/20068; G06T 2207/30; G06T 2207/30004; G06T 2207/30008; G06T 2207/30052; G06T 2211/00; G06T 2211/40

See application file for complete search history.

(56) References Cited

U.S. PATENT DOCUMENTS

2010/0208864 A1*   8/2010   Soejima ................ A61B 6/032
                        378/14
2014/0093154 A1*   4/2014   Penenberg ............ G06F 19/321
                        382/132

* cited by examiner

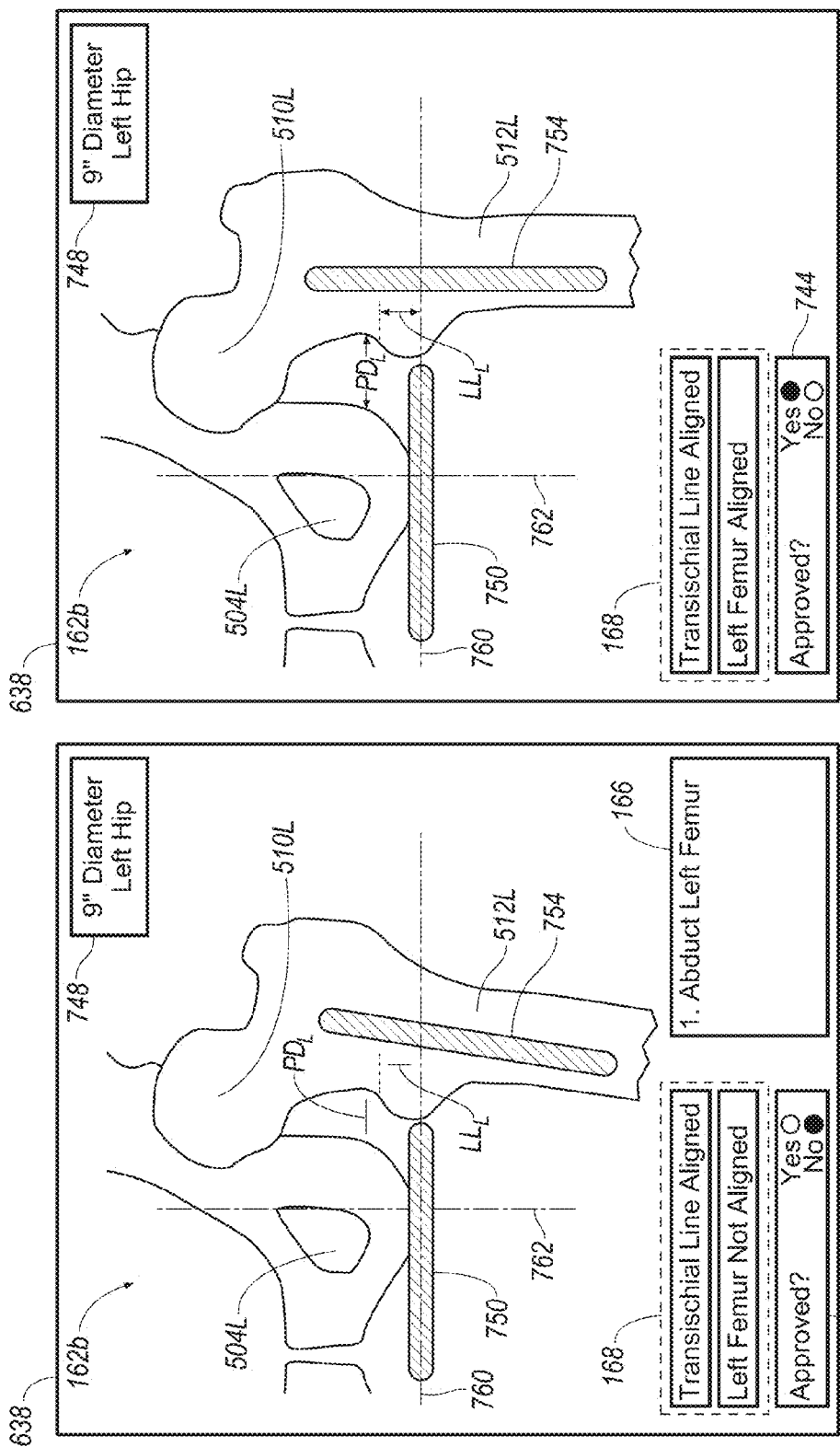

SYSTEM AND METHOD FOR ADJUSTING ALIGNMENT OF A BODY PART WITH AN IMAGING APPARATUS

CROSS REFERENCE TO RELATED APPLICATIONS

This U.S. patent application claims priority under 35 U.S.C. § 119(e) to U.S. Provisional Application 61/898,228, filed on Oct. 31, 2013, the contents of which are hereby incorporated by reference.

TECHNICAL FIELD

This disclosure relates to an alignment system and method for aligning body parts during surgery.

BACKGROUND

Total hip replacement is a procedure that is performed over 600,000 times every year worldwide, and up to 350,000 times per year in the United States alone. These procedures involve removing bone and cartilage from the diseased hip and replacing it with metal and plastic to give the patient a smooth articulating and long-lasting hip. Intra-operatively, the surgeon balances the unique bony anatomy of the patient with the limited implant sizing and shape variations made available by each of the manufacturers. To optimize the performance of the hip, the surgeon needs to balance the soft tissue envelope around the hip as well as the mechanical balance of the hip. Achieving this balance within a defined three-dimensional space drives the use of imaging devices, such as intraoperative C-arm x-rays.

An x-ray device outputs images of the patient's pelvic area, the surgeon begins evaluating the leg length, pelvic distance, and cup inclination visually. The hip replacement procedure includes a series of steps that require assessment before moving to the next step. While the intra-operative x-ray is one of the most valuable tools used to perform this assessment, the patient and the position of the x-ray device may unfortunately change during each step requiring a re-registration prior to utilizing the x-ray device. A variation of even a small amount from an optimal position can change the stability, mechanical balance, and potentially the longevity of the hip replacement. Thus, the accuracy of the x-ray image and the analysis thereof are very important stages of the procedure.

SUMMARY

One aspect of the disclosure provides a method including obtaining an image of a center of a pelvis of a patient captured by an imaging device and analyzing the image of the pelvis center to determine whether or not the pelvis center is aligned with the imaging device. When the pelvis center is not aligned with the imaging device, the method includes determining one or more alignment instructions for aligning the pelvis center with the imaging device by the computing device and transmitting the analyzed image of the pelvis center and the one or more pelvis alignment instructions to a user device in communication with the computing device. the user device executes a graphical user interface for displaying the analyzed image and one or more pelvis alignment instructions.

Implementations of the disclosure may include one or more of the following optional features. In some implementations, when the computing device analyzes the captured image of the pelvis center, the computing device identifies a horizontal pelvis line and a symphysis pubis of the pelvis within the image of the pelvis center and determines whether the horizontal pelvis line is aligned with a center horizontal axis of a field of view of the imaging device and whether the symphysis pubis is aligned with a center vertical axis of the field of view. In some examples, when at least one of the horizontal pelvis line or the symphysis pubis are not aligned, the computing device determines the pelvis center is not aligned with the imaging device. Additionally or alternatively, when the computing device analyzes the captured image of the pelvis center, the computing device identifies first and second obturator foramens of the pelvis within the image of the pelvis center and determines whether the first and second obturator foramens are substantially equal in at least one of size, shape, or symmetry with respect to a symphysis pubis. In some examples, the first and second obturator foramens are not substantially equal in at least one of size, shape, or symmetry with respect to a symphysis pubis, the computing device determines the pelvis center is not aligned with the imaging device. In some implementations, the computing device registers a transischial alignment graphic to the analyzed image of the pelvis center. The transischial alignment graphic may include a first color when the horizontal pelvis line and the center horizontal axis are aligned and may include a second color when the horizontal pelvis line and the center horizontal axis are not aligned.

In some examples, the computing device obtains an image of a first hip of the patient captured by the imaging device and analyzes the captured image of the first hip to determine whether or not the first hip is aligned with the imaging device. In some examples, when the first hip is not aligned with the imaging device, the computing device determines one or more hip alignment instructions for aligning the first hip with the imaging device and transmits the analyzed image of the first hip and the one or more first hip alignment instructions to the user device for display upon the graphical user interface. In some implementations, when the first hip is aligned with the imaging device, the computing device obtains an image of a second hip of the patient captured by the imaging device and analyzes the captured image of the second hip to determine whether or not the second hip is aligned with the imaging device. In some examples, when the second hip is not aligned with the imaging device, the computing device determines one or more second hip alignment instructions for aligning the second hip with the imaging device and transmits the analyzed image of the second hip and the one or more second hip alignment instructions to the user device for display upon the graphical user interface. The first hip may include a non-operative hip and the second hip may include a replacement hip.

In some implementations, when analyzing the captured image of the first hip, the computing device identifies a horizontal pelvis line and a first femur of the first hip within the image of the first hip, determines whether the horizontal pelvis line is aligned with a center horizontal axis of a field of view of the imaging device and whether the first femur is substantially perpendicular to the center horizontal axis, and when at least one of the horizontal pelvis line is not aligned with the center horizontal axis or the first femur is not substantially perpendicular to the center horizontal axis, determines the first hip is not aligned with the imaging device. In some examples, the computing device registers a transischial alignment graphic to the analyzed image of the pelvis center. For example, the transischial alignment graphic may include a first color when the horizontal pelvis line and the center horizontal axis are aligned and may include a second color when the horizontal pelvis line and the center horizontal axis are not aligned. In some examples, the computing device registers a vertical first femur alignment graphic to the analyzed image of the first hip. For example, the vertical first femur alignment graphic may include the first color when the first femur and the center horizontal axis are substantially perpendicular and may include the second color when the first femur and the center horizontal axis are not substantially perpendicular.

In some examples, when analyzing the captured image of the second hip, the computing device identifies a horizontal pelvis line and a second femur of the second hip within the image of the second hip, determines whether the horizontal pelvis line is aligned with a center horizontal axis of a field of view of the imaging device and whether the second femur is substantially perpendicular to the center horizontal axis, and when at least one of the horizontal pelvis line is not aligned with the center horizontal axis or the second femur is not substantially perpendicular to the center horizontal axis, determines the second hip is not aligned with the imaging device. In some examples, the computing device registers a transischial alignment graphic to the analyzed image of the pelvis center. For example, the transischial alignment graphic may include a first color when the horizontal pelvis line and the center horizontal axis are aligned and may include a second color when horizontal pelvis line and the center horizontal axis are not aligned. In some examples, the computing device registers a vertical second femur alignment graphic to the analyzed image of the first hip. For example, the vertical second femur alignment graphic may include the first color when the second femur and the center horizontal axis are substantially perpendicular and may include the second color when the second femur and the center horizontal axis are not substantially perpendicular.

In some examples, the hip manager transmits one of the pelvis center, the first hip, or the second hip alignment instructions to the imaging device. The imaging device may include at least one motor for adjusting a position of the imaging device and a motor controller in communication with the motor. In some examples, the motor controller, when executing the one of the pelvis center, the first hip, or the second hip alignment instructions, causes the motor to adjust the position of the imaging device based on the one of the pelvis center, the first hip, or the second hip alignment instructions.

In some implementations, when the computing device determines images captured by the imaging device of the pelvis center, a first hip, and a second hip are all aligned with the imaging device, the computing device fuses the previously analyzed images of the pelvis center, the first hip, and the second hip to generate a fused image, calculates a leg length measurement, a pelvic distance measurement, and a major cup diameter angle of the second hip within the fused image, determines whether or not the leg length measurement, the pelvic distance measurement, and the cup inclination angle of the second hip are acceptable, and transmits the fused image, the leg length measurement, the pelvic distance measurement, and the cup major cup diameter of the second hip to the user device for display upon the graphical user interface. In some examples, when determining whether or not the leg length measurement, the pelvic distance measurement, and the major cup diameter angle of the second hip are acceptable, the computing device determines the leg length measurement of the second hip is acceptable when the leg length measurement is within a predetermined leg length range, determines the pelvic distance measurement of the second hip is acceptable when the pelvic distance measurement is within a predetermined pelvic distance range, and determines the major cup diameter angle of the second hip is acceptable when the major cup diameter angle is within a predetermined major cup diameter angle range. In other examples, the computing device calculates a leg length measurement and a pelvic distance measurement of the first hip within the fused image, determines the leg length measurement of the second hip is acceptable when a magnitude of a leg length difference between the first and second hips is less than a leg length difference threshold, determines the pelvic distance measurement of the second hip is acceptable when a magnitude of a femoral offset based on a difference between the pelvic distances of the first and second hips is less than a femoral offset threshold, and determines the major cup diameter angle of the second hip is acceptable when the major cup diameter angle is within a predetermined cup major cup diameter range. In some examples, the computing device stores the fused image within a non-transitory data store in communication with the computing device. In some implementations, the imaging device includes a C-arm x-ray imaging device.

Another aspect of the disclosure provides a system including an imaging device and one or more alignment processing devices in communication with the imaging device and executing an alignment service. The alignment service obtains an image of a center of a pelvis of a patient captured by an imaging device and analyzes the image of the pelvis center to determine whether or not the pelvis center is aligned with the imaging device. When the pelvis center is not aligned with the imaging device, the alignment service determines one or more alignment instructions for aligning the pelvis center with the imaging device and transmits the analyzed image of the pelvis center and the one or more pelvis alignment instructions to a user device in communication with the alignment service. The user device executes a graphical user interface for displaying the analyzed image and one or more pelvis alignment instructions.

This aspect may include one or more of the following optional features. In some implementations, when the alignment service analyzes the captured image of the pelvis center, the alignment service identifies a horizontal pelvis line and a symphysis pubis of the pelvis within the image of the pelvis center and determines whether the horizontal pelvis line is aligned with a center horizontal axis of a field of view of the imaging device and whether the symphysis pubis is aligned with a center vertical axis of the field of view. In some examples, when at least one of the horizontal pelvis line or the symphysis pubis are not aligned, the alignment service determines the pelvis center is not aligned with the imaging device. Additionally or alternatively, when the alignment service analyzes the captured image of the pelvis center, the alignment service identifies first and second obturator foramens of the pelvis within the image of the pelvis center and determines whether the first and second obturator foramens are substantially equal in at least one of size, shape, or symmetry with respect to a symphysis pubis. In some examples, the first and second obturator foramens are not substantially in at least one of size, shape, or symmetry with respect to a symphysis pubis, the alignment service determines the pelvis center is not aligned with the imaging device. In some implementations, the alignment service registers a transischial alignment graphic to the analyzed image of the pelvis center. The transischial alignment graphic may include a first color when the horizontal pelvis line and the center horizontal axis are aligned and may include a second color when the horizontal pelvis line and the center horizontal axis are not aligned.

In some examples, the alignment service, at the one or more alignment processing devices, obtains an image of a first hip of the patient captured by the imaging device and analyzes the captured image of the first hip to determine whether or not the first hip is aligned with the imaging device. In some examples, when the first hip is not aligned with the imaging device, the alignment service, at the one or more alignment processing devices, determines one or more hip alignment instructions for aligning the first hip with the imaging device and transmits the analyzed image of the first hip and the one or more first hip alignment instructions to the user device for display upon the graphical user interface. In some implementations, when the first hip is aligned with the imaging device, the alignment service, at the one or more alignment processing devices, obtains an image of a second hip of the patient captured by the imaging device and analyzes the captured image of the second hip to determine whether or not the second hip is aligned with the imaging device. In some examples, when the second hip is not aligned with the imaging device, the alignment service, at the one or more alignment processing devices, determines one or more second hip alignment instructions for aligning the second hip with the imaging device and transmits the analyzed image of the second hip and the one or more second hip alignment instructions to the user device for display upon the graphical user interface. The first hip may include an non-operative hip and the second hip may include a replacement hip.

In some implementations, when analyzing the captured image of the first hip, the alignment service, at the one or more alignment processing devices, identifies a horizontal pelvis line and a first femur of the first hip within the image of the first hip, determines whether the horizontal pelvis line is aligned with a center horizontal axis of a field of view of the imaging device and whether the first femur is substantially perpendicular to the center horizontal axis, and when at least one of the horizontal pelvis line is not aligned with the center horizontal axis or the first femur is not substantially perpendicular to the center horizontal axis, determines the first hip is not aligned with the imaging device. In some examples, the alignment service, at the one or more alignment processing devices, registers a transischial alignment graphic to the analyzed image of the pelvis center. For example, the transischial alignment graphic may include a first color when the horizontal pelvis line and the center horizontal axis are aligned and may include a second color when the horizontal pelvis line and the center horizontal axis are not aligned. In some examples, the alignment service, at the one or more alignment processing devices, registers a vertical first femur alignment graphic to the analyzed image of the first hip. For example, the vertical first femur alignment graphic may include the first color when the first femur and the center horizontal axis are substantially perpendicular and may include the second color when the first femur and the center horizontal axis are not substantially perpendicular.

In some implementations, the system further includes one or more hip parameter measurement processing devices in communication with the alignment service and executing a hip parameter measurement service. In some examples, when the alignment service, at the one or more alignment processing devices, determines images captured by the imaging device of the pelvis center, a first hip, and a second hip are all aligned with the imaging device, the hip parameter measurement service, at the one or more hip parameter processing devices, fuses the previously analyzed images of the pelvis center, the first hip, and the second hip to generate a fused image, calculates a leg length measurement, a pelvic distance measurement, and a cup inclination angle of the second hip within the fused image, determines whether or not the leg length measurement, the pelvic distance measurement, and the cup inclination angle of the second hip are acceptable, and transmits the fused image, the a leg length measurement, the pelvic distance measurement, and the cup inclination angle of the second hip to the user device for display upon the graphical user interface. In some examples, when determining whether or not the leg length measurement, the pelvic distance measurement, and the cup inclination angle of the second hip are acceptable, the hip parameter measurement service, at the one or more hip parameter processing devices, determines the leg length measurement of the second hip is acceptable when the leg length measurement is within a predetermined leg length range, determines the pelvic distance measurement of the second hip is acceptable when the pelvic distance measurement is within a predetermined pelvic distance range, and determines the cup inclination angle of the second hip is acceptable when the cup inclination angle is within a predetermined cup inclination angle range. In other examples, the hip parameter measurement service, at the one or more hip parameter measurement processing devices, calculates a leg length measurement and a pelvic distance measurement of the first hip within the fused image, determines the leg length measurement of the second hip is acceptable when a magnitude of a leg length difference between the first and second hips is less than a leg length difference threshold, determines the pelvic distance measurement of the second hip is acceptable when a magnitude of a femoral offset based on a difference between the pelvic distances of the first and second hips is less than a femoral offset threshold, and determines the cup inclination angle of the second hip is acceptable when the cup inclination angle is within a predetermined cup inclination angle range.

In some examples, the hip alignment service, at the one or more hip alignment processing devices, transmits one of the pelvis center, the first hip, or the second hip alignment instructions to the imaging device. The imaging device may include at least one motor for adjusting a position of the imaging device and a motor controller in communication with the motor. In some examples, the motor controller, when executing the one of the pelvis center, the first hip, or the second hip alignment instructions, causes the motor to adjust the position of the imaging device based on the one of the pelvis center, the first hip, or the second hip alignment instructions.

In some examples, the system further includes one or more reporting processing devices in communication with the hip parameter measurement service and executing a reporting service, the reporting service stores the fused image within a non-transitory data store in communication with the computing device. In some implementations, the imaging device includes a C-arm x-ray imaging device.

The details of one or more implementations of the disclosure are set forth in the accompanying drawings and the description below. Other aspects, features, and advantages will be apparent from the description and drawings, and from the claims.

DESCRIPTION OF DRAWINGS

FIGS. 7F and 7G show analyzed images captured by the imaging device positioned over a left non-operative hip of a patient.

Like reference symbols in the various drawings indicate like elements.

DETAILED DESCRIPTION

Figure 1:
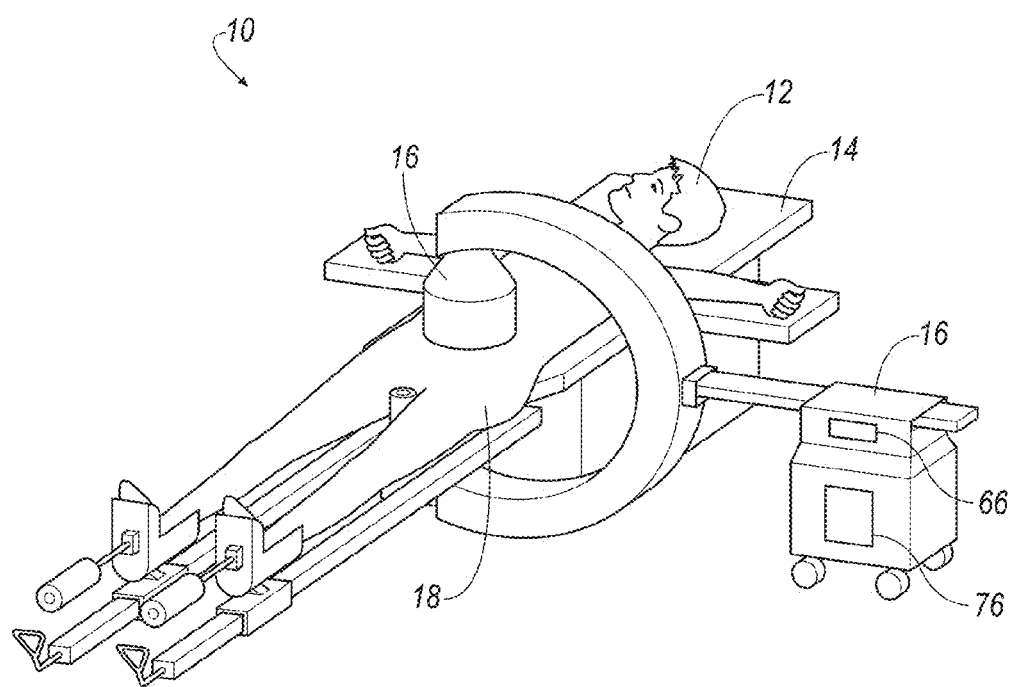
FIG. 1 shows an example operating room environment

FIG. 1 shows an example operating room environment 10. In the example shown, a patient 12 is on an operating table 14 in a supine position. An imaging device 16 captures one or more images of a pelvic area/hip 18 (hereinafter "pelvic area") of the patient 12. For instance, if the patient 12 is receiving a hip replacement surgery, the imaging device 16 captures images of the pelvic area 18 of the patient 12 so that the surgeon performing the surgery can view internal images of this area during the operation. As shown, the imaging device 16 is a C-arm x-ray device. Any other suitable imaging device 16 may be used, however, such as a fluoroscope and the like. While this disclosure will reference imaging device 16 as a C-arm x-ray device, it is to be understood that the claimed device and methods should not be so limited to the exemplary C-arm x-ray device unless specifically expressed. In the case of a C-arm x-ray device, the imaging device 16 may have a nine inch tube or a twelve inch tube, among other possibilities. In an implementation, the imaging device 16 may be connected to a display device (e.g., display 436 of FIG. 4), such that a user 40 can command the imaging device 16 to capture an image. As used herein, the term "user" 40 can refer to a surgeon, an x-ray technician, or any other personnel associated with the surgery. Upon receiving a command, the imaging device 16 captures an image 160 and transmits the image 160 to the display device 436. The display device 436 can display the captured image 160. The imaging device 16 may include a motor controller 66 and at least one motor 76 in communication with the motor controller 66 for adjusting a position of the imaging device 16. For instance, adjusting the position of the imaging device 16 includes translating and rotating the imaging device 16 along any one of five axis. Described in greater detail below with reference to process 700 (FIG. 7), the motor controller 66 may receive and execute adjustment instructions from a hip manager 450 (FIG. 4) that causes the motor 76 to align the imaging device 16 with one of a pelvis center, left hip, or right hip of the patient's 12 pelvic area 18.

Figure 2:
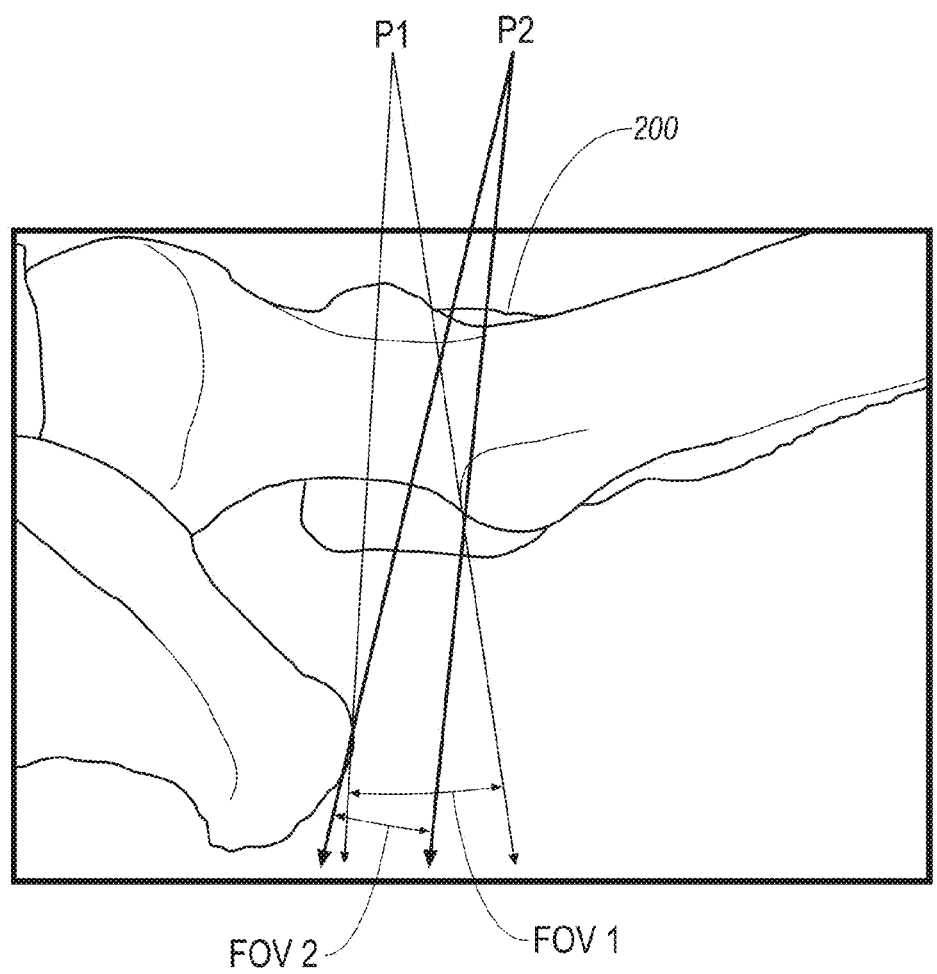
FIG. 2 is an example of parallax.

One issue that can arise when using an imaging device 16 is that when the imaging device 16 is repositioned at another location with respect to the patient 12, cross-parallax and/or parallax can occur and may thereby distort the spatial relationships between objects in the field of view of the imaging device 16. FIG. 2 illustrates an example of cross-parallax. Parallax can refer to inconsistencies in images of an object 200 that result from viewing an object 200 from different viewing positions P1, P2. For instance, cross-parallax can refer to inconsistent distances between different parts of the hip and pelvis when viewed from different viewing angles. In the illustrated example, the imaging device 16 captures images from at least two positions and the drawings illustrate a first position, P1, and a second position, P2. As shown, the field of view FOV1 of the imaging device 16 at the first position P1 captures the object 200 at a different angle than the field of view FOV2 of the imaging device 16 from the second position P2. The foregoing situation can cause cross-parallax, which may hamper the surgeon's ability to accurately measure the pelvic distance, leg length, cup anteversion angle, or cup inclination angle of the pelvis.

Figure 3:
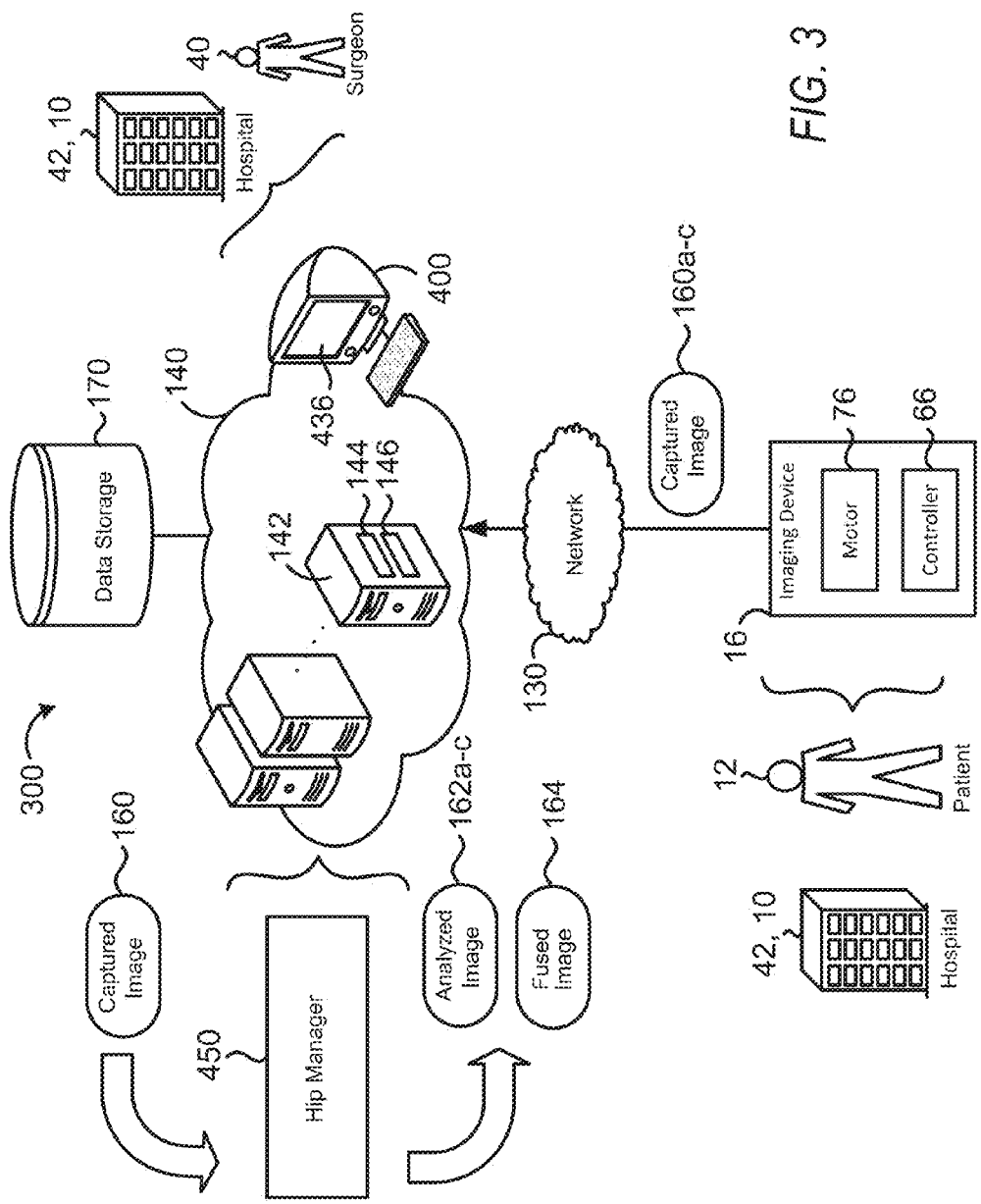
FIG. 3 is a schematic view of an exemplary system for aligning a pelvic area of a patient with an imaging device.

Referring to FIG. 3, in some implementations, a hip alignment system 300 includes an imaging device 16 associated with a patient 12, who may be within an operating room 10 of a hospital 42, clinic or surgery facility. In some examples, the imaging device 16 is a C-arm x-ray device 16 as discussed above with reference to FIG. 1. The imaging device 16 is configured to capture one or more images 160 (e.g., x-ray images) of the pelvic area 18 of the patient 12. The imaging device 16 may capture a first image 160a corresponding to a center of a pelvic area/pelvis 500 (FIG. 5) of the patient 12, a second image 160b corresponding to a left hip 510L (FIG. 5) of the patient 12, and a third image 160c corresponding to a right hip 510 R (FIG. 5) of the patient 12. In some implementations, the imaging device 16 implements an imaging computing device 66 for generating a DICOM (Digital Imaging and Communications in Medicine) compliant image 160 of the pelvic area 18 of the patient 12. The imaging computing device 66 is additionally operative as the motor controller 66 for controlling the one or more motors 76 to translate and/or rotate the position of the imaging device with respect to the patient 12.

The imaging device 16 is in communication, via a network 130, with a remote system 140. The remote system 140 may be a distributed system (e.g., cloud environment) having scalable/elastic resources 142. The resources 142 may include computing resources 144 and/or storage resources 146. In some examples, the computing resources 144 generate the DICOM compliant image 160 of the pelvic area 18 of the patient 12. The distributed system 140 includes a user device 400 associated with a user 40 such as a surgeon or other medical professional, who may be at, or near the operating room environment 10 within the surgery facility located at a clinic or hospital 42. In some implementations, the remote system 140 executes a hip manager 450 that analyzes the image 160 captured by the imaging device 16 and generates an analyzed image 162 analyzing alignment of the pelvic area 18 of the patient 12 for the surgeon 40 to view upon a display 436 executing on the user device 400. For instance, the hip manager 450 may generate a first analyzed image 162a analyzing alignment of the center of the pelvis 500, a second analyzed image 162b analyzing alignment of the left hip 510L of the patient 12, and a third image 162 analyzing alignment of the right hip 510R of the patient 12. In some examples, when any one of the analyzed images 162a-c are indicated as not being aligned with the imaging device 16, the hip manager 450 may generate alignment instructions that may be displayed for the surgeon 40 and further transmitted to the motor controller 66 in communication with the hip manager 450. The motor controller 66 may execute the alignment instructions 166 and cause the motor 76 to adjust the position of the imaging device 16 for acceptable alignment with the pelvic area 18.

In some implementations, when each of the analyzed images 162a-c are indicated as being aligned, the hip manager 450 fuses the analyzed images 162a-c to generate a fused image 164 for the surgeon 40 to view upon the display 436 executing on the user device 400. The fused image 164 is indicative of a parallax and cross-parallax free image for enabling accurate measurements of leg length, pelvic distance, femoral offset, cup anteversion angle, cup inclination angle, and/or major cup diameter angle of the pelvic area 18 of the patient 12.

In some examples, the remote system 140 communicates with non-transitory data storage 170. In some implementations, the remote system 140 and the non-transitory data storage 170 correspond to a hospital information system (HIS) for analyzing and storing the captured, analyzed and fused images 160, 162, 164, respectively. For example, the HIS may be associated with a picture arching communication system (PACS) and/or a radiation information system (RIS). The network 130 may include various types of networks, such as a wired network, a local area network (LAN), wide area network (WAN), and/or the Internet.

Although the network 130 may represent a long range network (e.g., Internet or WAN), in some implementations, the network 130 includes a shorter range network, such as a local area network (LAN) or a wired network. In some implementations, the network 130 uses standard communications technologies and/or protocols. Thus, the network 130 can include links using technologies, such as Ethernet, Wireless Fidelity (WiFi) (e.g., 802.11), worldwide interoperability for microwave access (WiMAX), 3G, Long Term Evolution (LTE), digital subscriber line (DSL), asynchronous transfer mode (ATM), InfiniBand, PCI Express Advanced Switching, etc. Similarly, the networking protocols used on the network 130 can include multiprotocol label switching (MPLS), the transmission control protocol/Internet protocol (TCP/IP), the User Datagram Protocol (UDP), the hypertext transport protocol (HTTP), the simple mail transfer protocol (SMTP), the file transfer protocol (FTP), etc. The data exchanged over the network 130 can be represented using technologies and/or formats including the hypertext markup language (HTML), the extensible markup language (XML), etc. In addition, all or some of the links can be encrypted using conventional encryption technologies, such as secure sockets layer (SSL), transport layer security (TLS), virtual private networks (VPNs), Internet Protocol security (IPsec), etc. In other examples, the network 130 can use custom and/or dedicated data communications technologies instead of, or in addition to, the ones described above.

Figure 4:
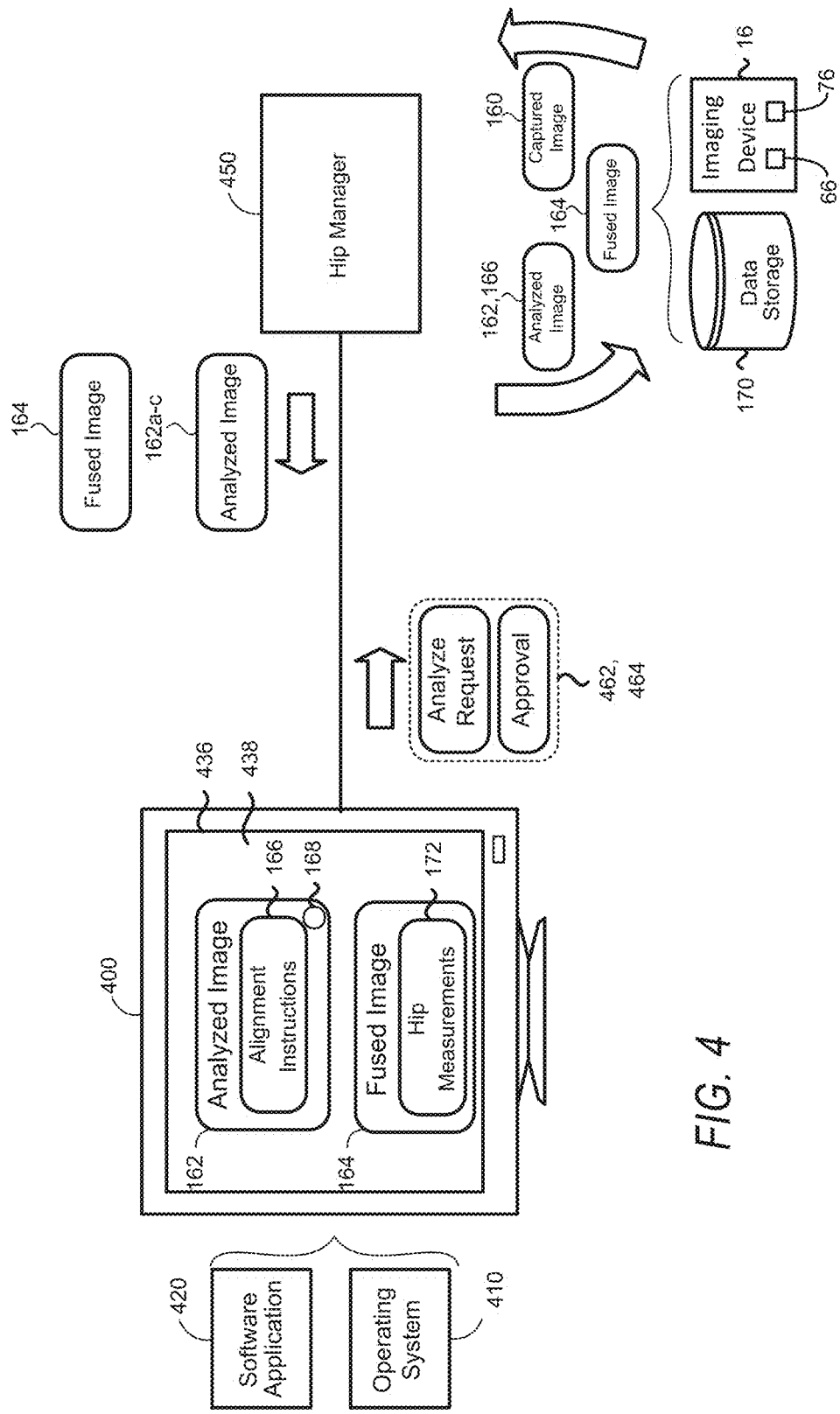
FIG. 4 is a schematic view of an exemplary system for aligning a pelvic area of a patient with an imaging device.

FIG. 4 shows an example user device 400 in communication with the hip manager 450. User devices 400 can be any computing devices such as, but not limited to, operating room workstations, laptops, smartphones and tablets. The user device 400 may use an operating system 410 that executes one or more software applications 420. A software application 420 may refer to computer software that, when executed by a computing device, causes the computing device to perform a task. In some examples, the software application 420 may be referred to as an "application", an "app", or a "program". Example software applications 420 include, but are not limited to, web-based applications, image processing applications, word processing applications, spreadsheet applications, messaging applications, media streaming applications, social networking applications, and games.

Applications 420 can be executed on a variety of different user devices 400. In some examples, applications 420 are pre-installed on the user device 400. In other examples, the user 40 may download and install applications 420 on the user device 400. In some implementations, the user device 400 executes a hip application 420 that communicates with the hip manager 450. In some examples, the hip manager 450 may transmit the analyzed image 162 through the network 130 to the user device 400 prompting the hip application 420 to render the analyzed image 162 for display upon a graphical user interface (GUI) 438 executing on the user device. In some examples, the hip manager 450 generates the analyzed image 162 in response to receiving an analyze request 462 from the user device 400. The hip application 420 may cause the user device 400 to transmit an approval message 464 to the hip manager 450 indicating that the corresponding analyzed image 162 is indicative of being aligned with the imaging device 16. In some examples, the user device 400 transmits first, second and third approval messages 464a, 464b and 464c, respectively, when each of the corresponding analyzed images 162a-c are indicative of being aligned with the imaging device 16.

In some implementations, the hip manager 450 transmits the fused image 164 through the network 130 to the user device 400 when all analyzed images 162a-c are indicative of being aligned with the imaging device 16. For example, for each approval message 464a-c that the hip manager 450 receives, the hip manager 450 may store the corresponding analyzed image 162a-c within the non-transitory data store 170. When all the approval messages 464a-c have been received, the hip manager 450 may retrieve and fuse the analyzed images 162a-c to generate the fused image 164. Since each of the analyzed images 162a-c included in the fused image 164 are indicative of being aligned, the fused image 164 may accurately depict the pelvic area 18 (e.g., pelvis 500) of the patient 12 without cross parallax and parallax such the hip manager 450 can accurately calculate the leg length, femoral offset, pelvic distance, cup anteversion angle, cup inclination angle, and/or major cup diameter angle measurements of the operative hip (e.g., 510R) of the patient 12.

In some implementations, the hip application 420 renders the analyzed image 162 for display upon a graphical user interface (GUI) 438 executing on the user device 400 when the hip manager 450 transmits the analyzed image 162 to the user device 400 through the network 130. The analyzed image 162 may include one or more alignment instructions 166 and one or more alignment indicators 168. The alignment instructions 166 may indicate to the user 40 one or more orientation changes to the patient 12 and/or imaging device 16 required for aligning the pelvic area 18 with the imaging device 16 to eliminate parallax and cross-parallax. The alignment instructions 166 may displayed upon the GUI 438 for the surgeon 42 to view. In some examples, the hip manager 166 further transmits the alignment instructions 166 to the imaging device 16 to cause adjustments in the position/orientation of the imaging device 16 for achieving alignment between the pelvic area 18 and the imaging device 16 without manual input from the surgeon 40. The one or more alignment indicators 168 may indicate to the user 40 whether or not the corresponding analyzed image 162 is indicative of the corresponding pelvic area 18 being aligned with the imaging device 16.

In some examples, the hip application 420 renders the analyzed image 162 for display upon the GUI 438 when hip manager 450 transmits the fused image 164 to the user device 400 through the network 130. The fused image 164 may include one or more hip parameter measurements 172 calculated by the hip manager 450 for the user 40 to view. In some examples, each hip parameter measurement 172 may be compared to a corresponding predetermined range of acceptable values. The user 40 may adjust the pelvic area 18 of the patient if one or more of the hip parameter measurements 172 are acceptable. In some examples, the hip application 420 causes the user device 400 to resend the analyze requests 462 after the user 40 adjusts the pelvic area 18 to ensure that each subsequent analyzed image 162 is indicative of the pelvic area 18 being aligned with the imaging device 16 such that the subsequent fused image 164 is parallax and cross-parallax free and the hip parameter measurements 172 can be accurately re-calculated. Thereafter, the hip manager 450 may transmit the subsequent fused image 164 and corresponding hip parameter measurements 172 to the user device 400 for display upon the GUI 438 such that the user 40 can verify whether the hip parameter measurements 172 are each within the corresponding predetermined range of acceptable values. In some examples each corresponding predetermined range of acceptable values is adjustable by the user 40 via the GUI 438.

Figure 5:
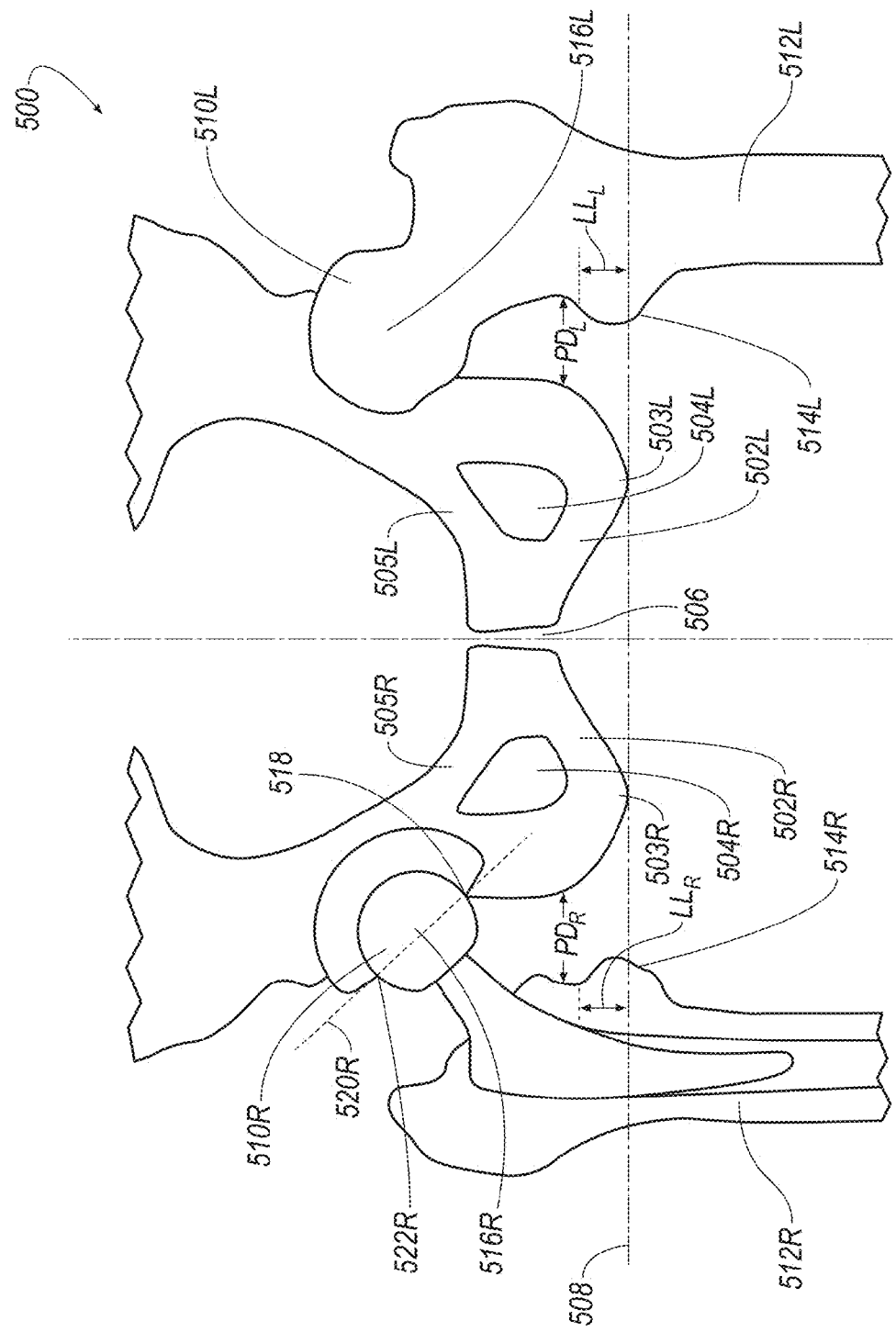
FIG. 5 shows anatomical landmarks of a pelvis.

FIG. 5 shows anatomical landmarks of a pelvis 500. In some examples, the hip manager 450 identifies the anatomical landmarks of the pelvis 500. The anatomical landmarks of the pelvis 500 include, inter alia, a right ischium 502R, a left ischium 502L, a right obturator foramen 504R, a left obturator foramen 504L, a right pubis bone 505R, a left pubis bone 505L, and a symphysis pubis line 506. A transischial line 508 is a horizontal pelvic line that extends tangentially from the lower portion 503L of the left ischium 502L to the lower portion 503R of the right ischium 502R. In the example shown, the left hip 510L is a non-operative hip and the right hip 510R is a replacement hip 510R corresponding to the operative hip. The hips 510R, 510L are coupled to the femurs 512R, 512L. The right femur 512R includes a right lesser trochanter 514R and a right femoral head 516R. The left femur 512L includes a left lesser trochanter 514L and a left femoral head 516L. In some examples, the horizontal pelvis line corresponds to the transischial line 508. In other examples, the horizontal pelvis line corresponds to a horizontal line that extends tangentially from an upper most point (e.g., tear drop) of the right obturator foramen 504R to an upper most point (e.g., tear drop) of the left obturator foramen 504L. In other examples, the horizontal pelvis line may correspond to any horizontal line that extends tangentially from one anatomical landmark located to the left of the symphysis pubis 506 to a corresponding anatomical landmark located to the right of the symphysis pubis 506.

When a hip replacement surgery is being performed, the surgeon 40 has many objectives, including ensuring hip parameter measurements 172 of the replacement hip 51OR are appropriate. The hip parameter measurements 172 may include a cup inclination angle 520R of the operative hip 510R, a leg length $LL_R$ of the operative hip 510R, and a pelvic distance $PD_R$ of the right femur 512R from the right ischium 502R (or other anatomical landmark of the pelvis (e.g., the symphysis pubis line 506)). The hip parameter measurements 172 may further include a cup anteversion angle 522R measuring a rotational angle of the cup 518 with respect to the horizontal pelvis line 508 (e.g., the transischial line). In some implementations, an angle of major diameter of the cup (major cup diameter angle) 518 to the horizontal pelvis line 508 (e.g., transischial line) can be determined based on the cup inclination angle 520R and the cup anteversion angle 522R. Additionally or alternatively, the hip parameter measurements 172 may include a cup inclination of the non-operative left hip 510L, a leg length $LL_L$ of the non-operative left hip 510L, and a pelvic distance $PD_L$ of the left femur 512L from the left ischium 502L(or other anatomical landmark of the pelvis (e.g., the symphysis pubis line 506)).

For a right hip 510R replacement, the pelvic distance $PD_R$ may be considered appropriate when it is approximately equal to the offset pelvic distance $PD_L$ of the left femur 512L to the left ischium 502L. The cup inclination of the operative hip 510R may be considered appropriate when the angle of the cup inclination line 520R tangentially intersecting ends of an acetabular shell 518 is within a range of 35 degrees to 45 degrees. The leg length of the operative hip 510R may be considered appropriate when the rise from the outermost point of the lesser trochanter 514R to the outermost point of the corresponding ischium 502R is approximately equal to the rise from the outermost point of the lesser trochanter 514L on the side of the non-operative hip 510L to the outermost point of the corresponding ischium 502L. The hip manager 450 aids the surgeon 40 in achieving these objectives and may identify the anatomical landmarks within the captured images 160. Anatomical landmarks may be identified by one or more of the following: detecting edges within the captured image 160, using feature recognition, texture recognition, or filtering techniques.

Figure 6:
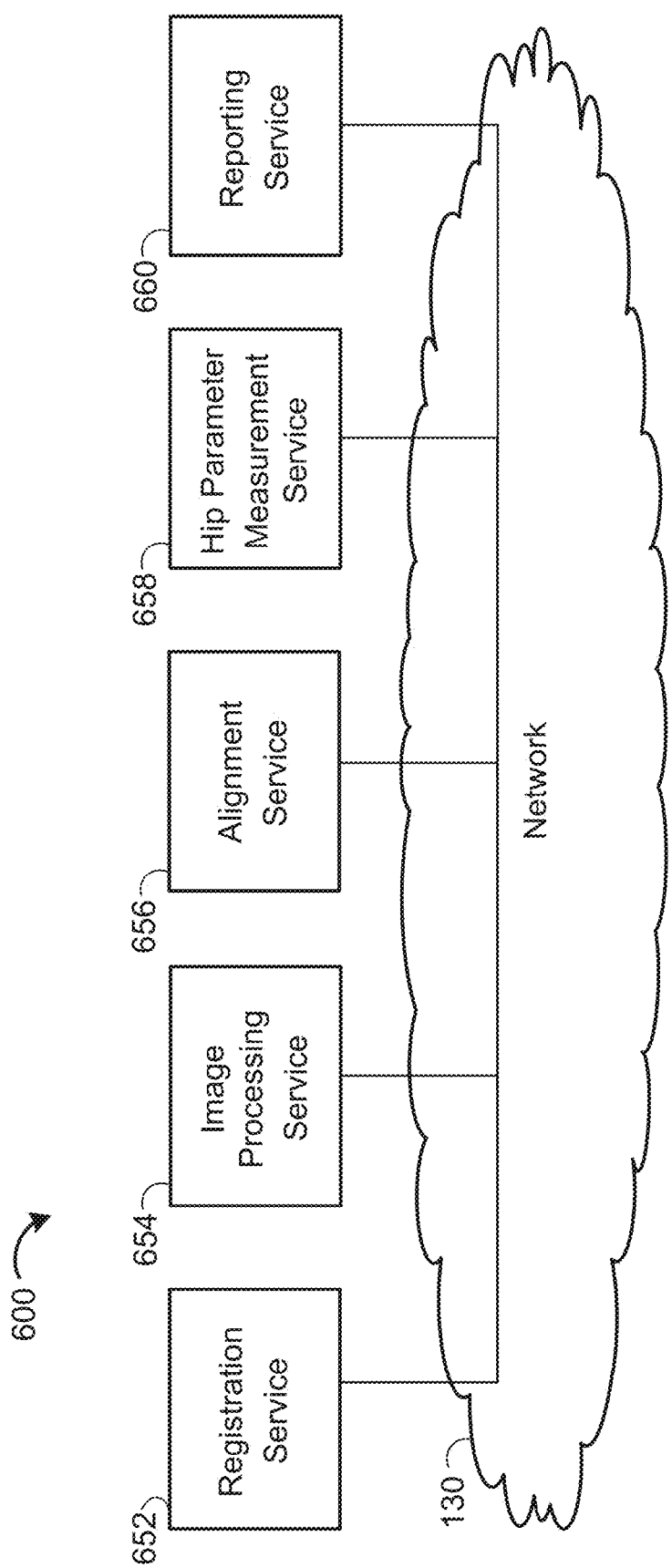
FIG. 6 shows example components of the system of FIGS. 2 and 3.

FIG. 6 shows example components 600 of the hip manager 450 of FIG. 3. The hip manager 450 includes a registration service 652, an image processing service 654, an alignment service 656, a hip parameter measurement service 658, and a reporting service 660. Each service 652, 654, 656, 658, 660 is in communication with the user device 400, the non-transitory data store 170, the imaging device 16 and the other services 652, 654, 656, 658, 660 via the network 130. Each service 652, 654, 656, 658, 660 may execute on a processor (e.g., computing resource 144).

The registration service 652 allows for the interaction of users 40 with the hip alignment system 300. The registration service 652 receives information inputted by the user 40 and allows the user 40 to retrieve previously inputted information stored in the non-transitory data store 170 (e.g., the HIS, the PACS, and/or the RIS). For instance, patient 12 information may be input to or retrieved by the registration service 652 including, but not limited to, the patient's name, medical history, surgical information and specifications of the operative hip (e.g., 610R) being implanted to the patient 12. Likewise, surgeon 40 preferences may be input to the registration service 652 via the GUI 438 including preferences for storing images 160, 162, 164 within the non-transitory data store and preferences for magnification (e.g., 9 inch, 12 inch wide or 12 inch narrow tubes) of the images 160 captured by the imaging device 16. The surgeon 40 may further input a desired sensitivity for identifying the anatomical landmarks within the captured image 160. For instance, a low sensitivity setting may require anatomical landmarks within the image 160 to be a close match, whereas a high sensitivity may require anatomical features within the image 160 to be a complete match. Adjusting the sensitivity may help facilitate workflow of the hip manager 450. In some examples, the user 40 adjusts the sensitivity differently for one or more of the anatomical landmarks. For instance, the sensitivity adjustments for identifying anatomical landmarks may be adjustable by the user 40 manipulating a slider bar graphic (or inputting a value) displayed upon the GUI 638. Example sensitivity adjustments for identifying anatomical landmarks may include, but are not limited to: magnification of the captured images 160 and marker sizing; equatorial ischium 502R, 502L position and confirmation; pelvis centered from left to right; obturator foramen 504R, 504L shape and area; femoral head 516R, 516R longitudinal position; femoral 512R, 512L shaft perpendicularity; femoral lesser trochanter 514R, 514L size, shape and peak location; and acetabular shell 518 teardrop location. The surgeon 40 may further input the basis for calculating the hip parameters measurements 172 and/or the desired values or range of values compared with each corresponding hip parameter measurement 172. As aforementioned, the hip parameter measurements 172 may include the cup inclination angle of the hip 510R, 510L, the leg length of the hip 510R, 510L and the pelvic distance $PD_R$, $PD_L$. In some examples, the hip parameter measurements 172 include the major cup diameter angle of the hip 510R with respect to the horizontal pelvis line 508 (e.g., transischial line). In some examples, a femoral offset is calculated, based on a difference between the pelvic distances $PD_R$, $PD_L$. Here, the femoral offset may be compared to a corresponding predetermined threshold or corresponding predetermined range of values. In some examples, a leg length difference between the leg lengths of the right and left hips 510R, 510L is calculated. Here, the leg length difference may be compared to a corresponding predetermined threshold or corresponding predetermined range of values. In some implementations, the registration service 652 may receive a user name and a password (e.g., at a login screen displayed upon the GUI 638 executing on the user device 400) to verify that a qualified and trained healthcare professional 40 (e.g., surgeon) is authorized to access the hip manager 450 and the hip alignment system 300.

The image processing service 654 allows for the analyzing of images 160 captured by the imaging device 16 for generating analyzed images 162, and for the generating of a fused image 164 that includes more than one analyzed image 162a-c fused together. The image processing service 654 receives a captured image 160 from the imaging device 16 or retrieves the captured image 160 from the non-transitory data store 170. In some examples, the captured image 160 is raw image data and the image processing service 654 generates a DICOM compliant image 160 on a computing resource 144 (e.g., processor). In other examples, the imaging device 16 provides the DICOM compliant image 160 on the processor 26. The image processing service 654 may further identify the anatomical landmarks when the images 160 are analyzed and include the identified anatomical landmarks in the analyzed image 162 transmitted to the user device 400.

The alignment service 656 and the image processing service 654 collectively execute a process 700 (e.g., an executable instruction set) on a processor (e.g., computing source 144) for analyzing the analyzed images 162a-c to determine whether or not the pelvis 500 (e.g., pelvic/hip area 18) of the patient 12 is aligned with the imaging device 16 to eliminate parallax and cross-parallax. For instance, the alignment service 656 may register alignment graphics upon the analyzed images to determine whether specified anatomical features identified are aligned with the imaging device 16. In some implementations, the alignment service 656 generates alignment instructions 166 indicating required changes in orientation to the patient 12 and/or imaging device 16 to achieve alignment between the pelvic area 18 and the imaging device 16. In some examples, the motor controller 66 executes the alignment instructions 166 to cause the motor 76 to adjust the position/orientation of the imaging device 16 to achieve acceptable alignment between the pelvic area 18 and the imaging device 16.

The hip parameter measurement service 658 and the imaging processing service 654 collectively execute a process 800 (e.g., an executable instruction set) on a processor (e.g., computing source 144) for generating and analyzing the fused image 164 to calculate the hip parameter measurements 172 and determine whether or not the hip parameter measurements 172 are acceptable. For instance, the hip parameter measurement service 658 may provide the calculated hip parameter measurements 172 to the user device 400 for display upon the GUI 638 and include an indicator as to whether or not each measurement 172 is acceptable.

The reporting service 660 may be in communication with a display 638 and provides information to the user 40 determined using the registration service 652, the image processing service 654, the alignment service 656, and the hip parameter measurement service 658. In some examples, the reporting service 660 stores each analyzed image 162 (and/or corresponding captured image 160) indicative of the pelvic area 18 being aligned with the imaging device 16 within the non-transitory data store 170. Additionally or alternatively, in some examples, the reporting service 660 stores the fused image 164 and corresponding approved hip parameter measurements 172 within the non-transitory data store 170.

Figure 7A:
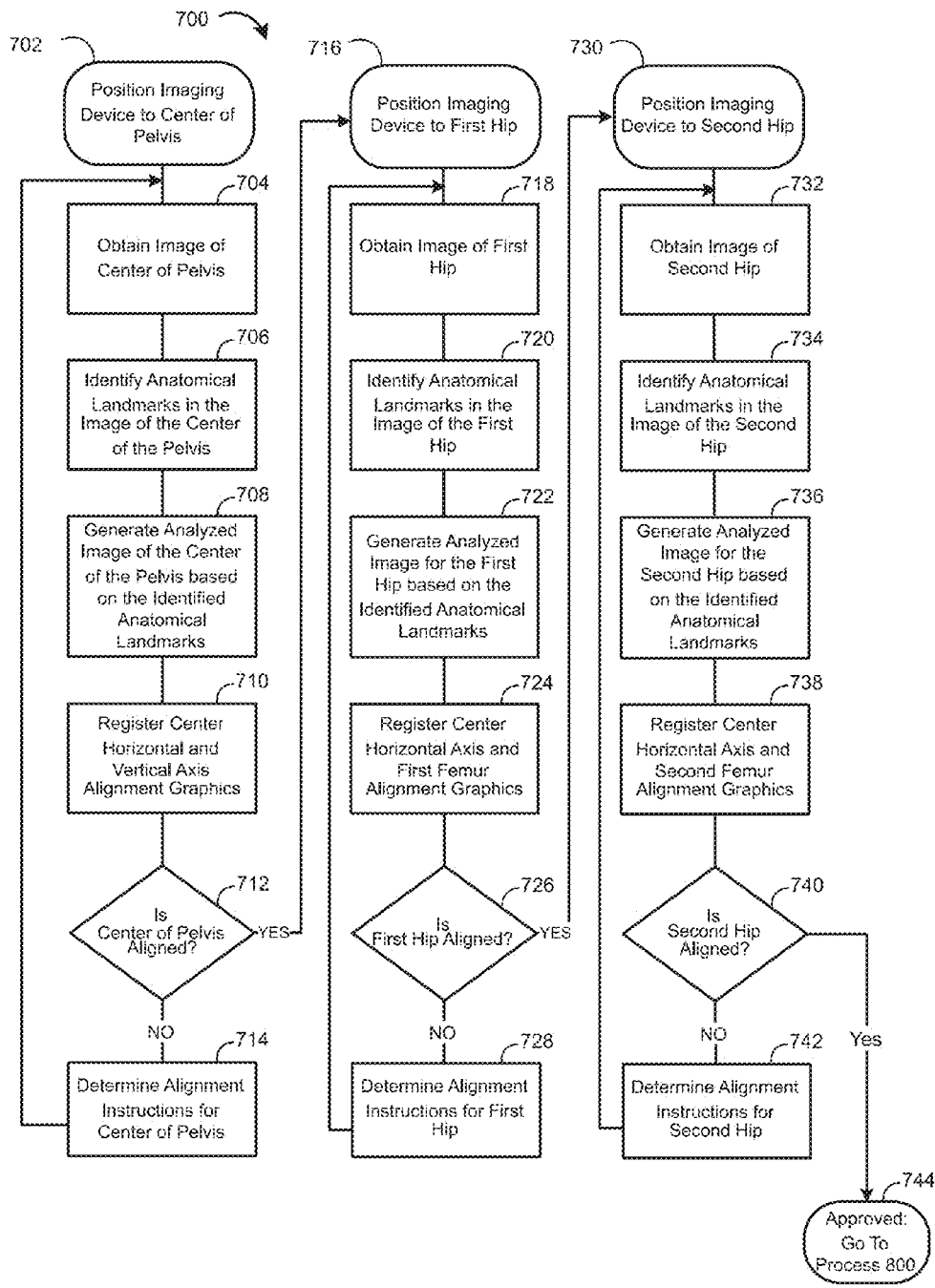
FIG. 7A shows an exemplary process for aligning a pelvic area of the patient using the system of FIGS. 2 and 3.
Figure 7B:
FIG. 7B shows an image captured by an imaging device positioned over a center of a pelvis of a patient.

Referring to FIGS. 3, 4 and 7A-7I, the process 700 obtains the captured images 160a-c input by the imaging device 16, generates the analyzed images 162a-c and determines whether or not the analyzed images 164 are aligned. The process 700 positions the imaging device 16 to the center of the pelvis 500 of the patient at block 702 and obtains the image 160a of the pelvic center 500 at block 704. In some examples, the hip manager 450 retrieves the captured image 160 of the pelvic center 500 from the non-transitory data store 170 using an analyze request 462 transmitted from the user device 400. In other examples, the hip manager 450 receives the captured image 160 of the pelvic center 500 from the imaging device 16. FIG. 7B shows an example captured image 160a of the pelvic center 500. A magnification marker 790 is shown. In some implementations, a size of the magnification marker 790 in the captured image 160a is compared with a known size of the magnification marker 790. If the size of the magnification marker 790 in the captured image 160a is not equal to the known size of the magnification marker 790, the magnification may be proportionally scaled based upon a difference in size between the captured image 160a and the known size. Thereafter, the scaled magnification may be utilized by process 800 (FIG. 8) when calculating hip parameter measurements. The process 700 identifies anatomical landmarks in the image 160 of the pelvic center 500 at block 706. The identified anatomical landmarks may include the anatomical landmarks shown in FIG. 5. In some implementations, a portion of the identified anatomical landmarks include the transischial line 508 and the symphysis pubis line 506 of the pelvis 500.

Figures 7C, 7D:
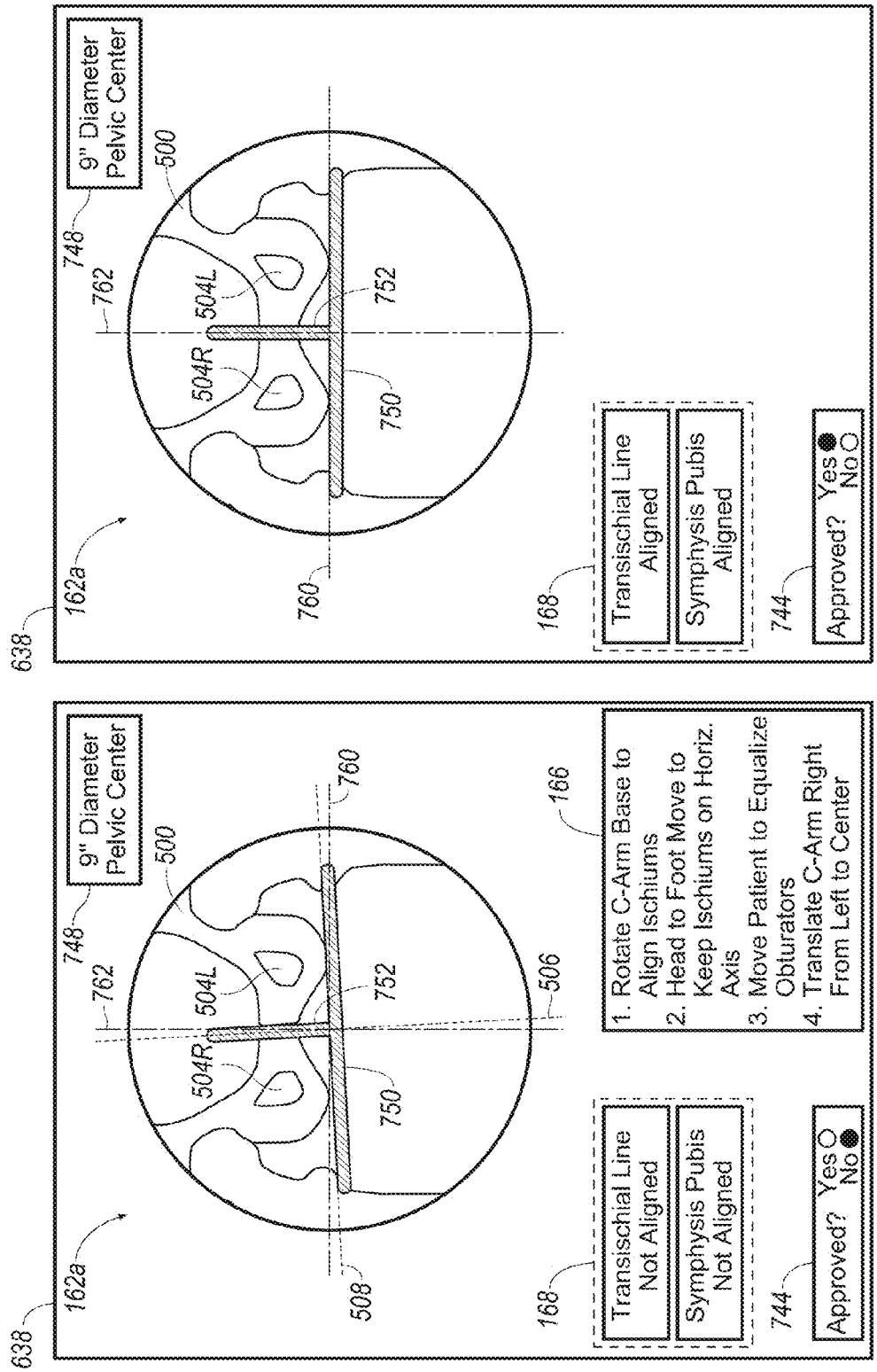
FIGS. 7C and 7D show analyzed images captured by the imaging device positioned over a center of a pelvis of a patient displayed upon a graphical user interface executing on a user device.

The process 700 generates an analyzed image 162a of the pelvic center based on the identified anatomical landmarks at block 708, and at block 710, registers a transischial alignment graphic 750 and a symphysis pubis alignment graphic 752 to the analyzed image 162a (FIGS. 7C and 7D). The transischial alignment graphic 750 corresponds to the horizontal pelvis line 508 and the symphysis pubis alignment graphic 752 corresponds to the symphysis pubis line 506. While the horizontal pelvis line is depicted as the transischial line 506 in the illustrated examples, the horizontal pelvis line may refer to an horizontal line that extends tangentially from one identified anatomical landmark positioned to the left of the symphysis pubis 506 to a corresponding identified anatomical landmark positioned to the right of the symphysis pubis 506. Accordingly, the illustrated examples when referring to the transischial line 506 are non-limiting, and may refer to any horizontal pelvis line. The process 700 further generates a center horizontal axis 760 of a field of view (FOV) of the imaging device 16 and a center vertical axis 762 of the FOV. The process 700, at block 712, determines whether or not the pelvic center is aligned with the imaging device 16. In some implementations, the pelvic center is aligned with the imaging device when the transischial line 508 is aligned with the center horizontal axis 760 and the symphysis pubis line 506 is aligned with the center vertical axis 762. When at least one of the transischial line 508 or the symphysis pubis line 506 are not aligned, the process 700 determines alignment instructions 166 for aligning the pelvis center at block 714. In some implementations, the process 700 transmits the alignment instructions 166 to the motor controller 66 to cause the motor 76 to adjust the position of the imaging device 16 based on the alignment instructions 166. When the transischial line 508 and the symphysis pubis line 506 are both aligned, the process 700 determines the pelvic center is aligned with the imaging device 16 and proceeds to block 716. The process 700 may transmit the analyzed image 162a to the user device 400 for display upon the GUI 438.

In some examples, process 700 determines whether the left and right obturator foramens 504L, 504R are substantially equal in at least one of size, shape, or symmetry with respect to the symphysis pubis 506 at block 712. For instance, when the obturator foramens 504L, 504R are not substantially equal in size, shape, or symmetry, the process 700 determines the pelvis center is not aligned with the imaging device 16 and proceeds to block 714 to determine alignment instructions 166.

FIG. 7C shows the analyzed image 162a displayed upon the GUI 438 executing on the user device 400 when the process 700 indicates at block 712 the pelvic center is not aligned with the imaging device 16. In the example shown, the GUI 438 displays imaging information 748 indicating a magnification of the analyzed image 162a (e.g., 9" Diameter) and position of the imaging device (e.g., the pelvic center), one or more alignment indicators 168, one or more alignment instructions 166, and approval commands 744 allowing the user 40 to approve or not approve the analyzed image 162a being displayed. In the example shown, the transischial alignment graphic 750 is not aligned with the center horizontal axis 760 and the symphysis pubis alignment graphic 752 is not aligned with the center vertical axis 762. In some implementations, the transischial alignment graphic 750 includes a first color (e.g., green) when the transischial line and the center horizontal axis are aligned and includes a second color (e.g., red) when the transischial line and the center horizontal axis are not aligned. In some implementations, the symphysis pubis alignment graphic 752 includes the first color when the symphysis pubis line 506 and the center vertical axis 762 are aligned and includes the second color when the symphysis pubis line 506 and the center vertical axis 762 are not aligned. In the example shown, the transischial alignment graphic 750 and the symphysis pubis alignment graphic 752 include the second color (e.g., red). The one or more alignment instructions 166 indicate instructions for aligning the pelvis center with the imaging device 16. In the example shown, the alignment instructions 166 include 1) Rotate C-Arm Base to Align Ischiums, 2) Head to Foot Move to Keep Ischiums on Horizontal Axis, 3) Move Patient to Equalize Obturators, and 4) Translate C-Arm From Left to Center.

Referring back to FIG. 7A, the process 700 reverts back to block 702 after the process determines the alignment instructions 166 at block 714 to determine if a subsequently captured image 160 of the pelvic center is aligned with the imaging device 16 after orientations of the patient 12 and/or imaging device 16 have been adjusted to achieve alignment. The process 700 iteratively repeats until the process 700 determines a subsequently analyzed image 162 indicates the pelvic center is aligned with the imaging device 16 at block 712.

FIG. 7D shows the analyzed image 162a displayed upon the GUI 438 executing on the user device 400 when the process 700 indicates at block 712 that the pelvic center is aligned with the imaging device 16. In the example shown, the transischial alignment graphic 750 and the symphysis pubis alignment graphic 752 include the first color (e.g., green) since the transischial line 508 is aligned with the center horizontal axis 760 and the symphysis pubis 506 is aligned with the center vertical axis 762, as indicated by the alignment indicators 168. No alignment instructions 166 are displayed upon the GUI 438 since the process 700 has determined that the pelvic center is aligned.

Figure 7E:
FIG. 7E shows an image captured by an imaging device positioned over a left non-operative hip of a patient.

The process 700 positions the imaging device 16 to the non-operative hip 510L (e.g., first hip) of the patient at block 716 and obtains the image 160b of the first hip 510L at block 718. Accordingly, the position of the imaging device 16 is translated to the right to now be positioned over the left hip 510L. In some implementations, the imaging device 16 is aligned such that the center vertical axis 706 of the FOV is directly over an upper most point (e.g., tear drop) of the left obturator foramen 504L. In other implementations, the imaging device 16 is aligned such that the center vertical axis 706 of the FOV is directly over the center of the left femoral head 516L; however, the imaging device 16 may be registered with any anatomical landmark to ensure alignment. In some examples, the hip manager 450 retrieves the captured image 160 of the first hip 510L from the non-transitory data store 170 using an analyze request 462b transmitted from the user device 400. In other examples, the hip manager 450 receives the captured image 160b of first hip 510L from the imaging device 16. FIG. 7E shows an example captured image 160b of the first hip 510L. The process 700 identifies anatomical landmarks in the image 160b of the first hip 510L at block 720. The identified anatomical landmarks may include the anatomical landmarks shown in FIG. 5. In some implementations, a portion of the identified anatomical landmarks include the transischial line 508 and the femur 512L of the pelvis 500.

The process 700 generates an analyzed image 162b of the first hip 510L based on the identified anatomical landmarks at block 722, and at block 724, registers a transischial alignment graphic 750 and a first femur alignment graphic 754 to the analyzed image 162b (FIGS. 7F and 7G). The transischial alignment graphic 750 corresponds to the transischial line 508 and the first femur alignment graphic 754 corresponds to the femur 512L. The process 700 further generates the center horizontal axis 760 of a field of view (FOV) of the imaging device 16. The process 700, at block 726, determines whether or not the first hip 510L is aligned with the imaging device 16. In some implementations, the first hip 510L is aligned with the imaging device 16 when the transischial line 508 is aligned with the center horizontal axis 760 and the first femur 512L is substantially perpendicular to the center horizontal axis 760. When at least one of the transischial line 508 or the first femur 512L are not aligned, the process 700 determines alignment instructions 166 for aligning the first hip 510L at block 728. In some implementations, the process 700 transmits the alignment instructions 166 to the motor controller 66 to cause the motor 76 to adjust the position of the imaging device 16 based on the alignment instructions 166. When the transischial line 508 and the first femur 512 are both aligned, the process 700 determines the first hip 510L is aligned with the imaging device 16 and proceeds to block 730. The process 700 may transmit the analyzed image 162b to the user device 400 for display upon the GUI 438.

FIG. 7F shows the analyzed image 162b displayed upon the GUI 438 executing on the user device 400 when the process 700 indicates at block 726 the first hip 510L is not aligned with the imaging device 16. The imaging information 748 indicates a new position of the imaging device 16 corresponding to the left first hip 510L. In the example shown, the transischial alignment graphic 750 is aligned with the center horizontal axis 760 and the first femur graphic 754 is not substantially perpendicular to the center horizontal axis 760. Accordingly, the transischial alignment graphic 750 may include the first color (e.g., green) since the transischial line 508 is aligned with the center horizontal axis 760, while the first femur graphic 754 may include the second color (e.g., red) since the first femur 512L is not substantially perpendicular with the center horizontal axis 760. The alignment instructions 166 displayed upon the GUI 438 include instructions for manipulating the first femur 512L to be substantially perpendicular to the center horizontal axis 760, e.g., Abduct Left Femur.

Referring back to FIG. 7A, the process 700 reverts back to block 718 after the process determines the alignment instructions 166 at block 728 to determine if a subsequently captured image 160 of the first hip 510L is aligned with the imaging device 16 after orientations of the patient 12 and/or imaging device 16 have been adjusted to achieve alignment (e.g., left femur 512L is abducted). The process 700 iteratively repeats until the process 700 determines a subsequently analyzed image 162 indicates the first hip 510L is aligned with the imaging device 16 at block 726.

FIG. 7G shows the analyzed image 162b displayed upon the GUI 438 executing on the user device 400 when the process 700 indicates at block 726 that the first hip 510L is aligned with the imaging device 16. In the example shown, the transischial alignment graphic 750 and the first femur graphic 754 include the first color (e.g., green) since the transischial line 508 is aligned with the center horizontal axis 760 and the first femur 512L is substantially perpendicular to the center horizontal axis 760, as indicated by the alignment indicators 168. No alignment instructions 166 are displayed upon the GUI 438 since the process 700 has determined that the first hip 510L is aligned.

Figure 7H:
FIG. 7H shows an image captured by an imaging device positioned over a right operative hip of a patient.

The process 700 positions the imaging device 16 to the operative hip 510R (e.g., second hip) of the patient at block 730 and obtains the image 160c of the second hip 510R at block 732. Accordingly, the position of the imaging device 16 is translated to the left to now be positioned over the right hip 510R. In some implementations, the imaging device 16 is aligned such that the center vertical axis 706 of the FOV is directly over an upper most point (e.g., tear drop) of the right obturator foramen 504R. In other implementations, the imaging device 16 is aligned such that the center vertical axis 706 of the FOV is directly over the center of the right hip 510R; however, the imaging device 16 may be registered with any anatomical landmark to ensure alignment. In some examples, the hip manager 450 retrieves the captured image 160 of the second hip 510R from the non-transitory data store 170 using an analyze request 462c transmitted from the user device 400. In other examples, the hip manager 450 receives the captured image 160c of second hip 510R from the imaging device 16. FIG. 7H shows an example captured image 160c of the second hip 510R. The process 700 identifies anatomical landmarks in the image 160c of the second hip 510R at block 734. The identified anatomical landmarks may include the anatomical landmarks shown in FIG. 5. In some implementations, a portion of the identified anatomical landmarks include the transischial line 508 and the femur 512R of the pelvis 500.

Figure 7I:
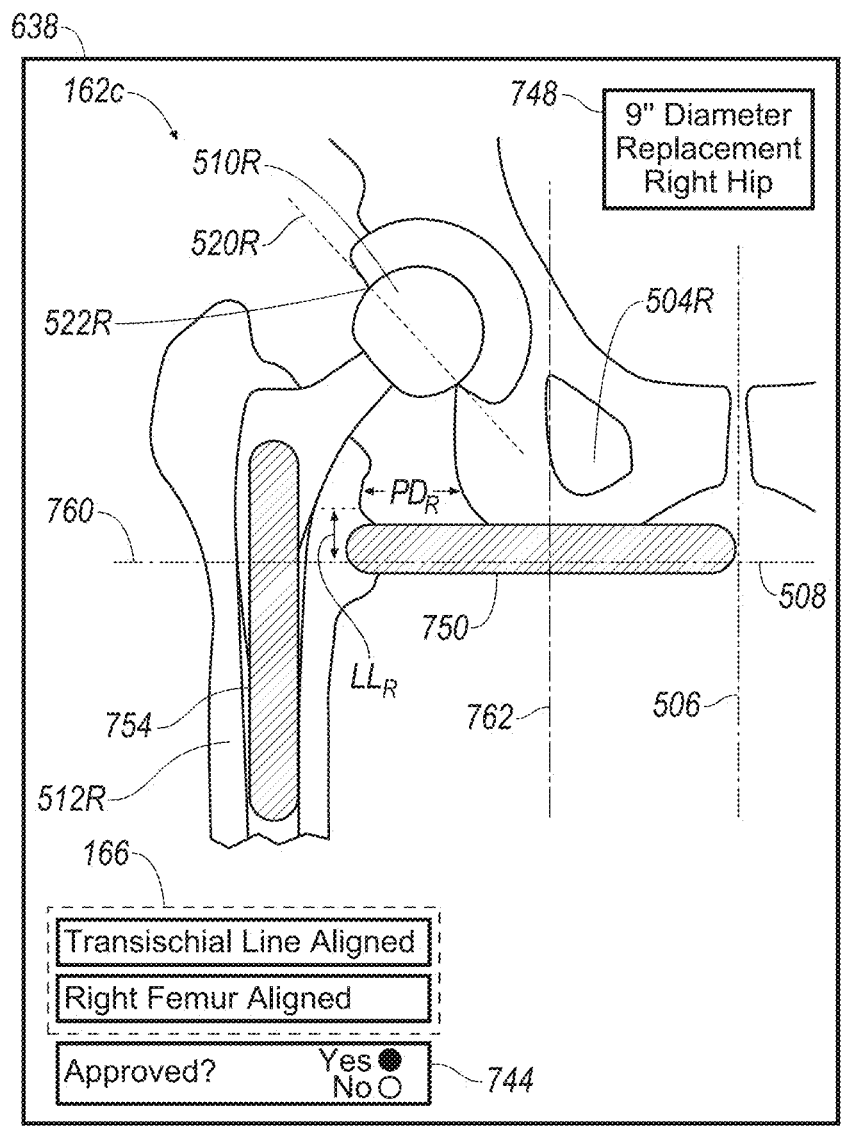
FIG. 7I shows an analyzed image captured by the imaging device positioned over a right operative hip of a patient.

The process 700 generates an analyzed image 162c of the second hip 510R based on the identified anatomical landmarks at block 736, and at block 738, registers a transischial alignment graphic 750 and a second femur alignment graphic 756 to the analyzed image 162c (FIG. 7I). The transischial alignment graphic 750 corresponds to the transischial line 508 and the second femur alignment graphic 756 corresponds to the first right femur 512R. The process 700 further generates the center horizontal axis 760 of the FOV of the imaging device 16. The process 700, at block 740, determines whether or not the second hip 510R is aligned with the imaging device 16. In some implementations, the second hip 510R is aligned with the imaging device 16 when the transischial line 508 is aligned with the center horizontal axis 760 and the second femur 512R is substantially perpendicular to the center horizontal axis 760. When at least one of the transischial line 508 or the second femur 512R are not aligned, the process 700 determines alignment instructions 166 for aligning the second hip 510R at block 742. In some implementations, the process 700 transmits the alignment instructions 166 to the motor controller 66 to cause the motor 76 to adjust the position of the imaging device 16 based on the alignment instructions 166. When the transischial line 508 and the second femur 512R are both aligned, the process 700 determines the second hip 510R is aligned with the imaging device 16 and proceeds to process 800 at block 744. Specifically, block 744 indicates that the process 700 has been approved due to the pelvic center, first hip 510L and second hip 510R all determined to be aligned with the imaging device 16. The process 700 may transmit the analyzed image 162c to the user device 400 for display upon the GUI 438.

FIG. 7I shows the analyzed image 162b displayed upon the GUI 438 executing on the user device 400 when the process 700 indicates at block 740 that the second hip 510R is aligned with the imaging device 16. In the example shown, the transischial alignment graphic 750 and the second femur graphic 756 include the first color (e.g., green) since the transischial line 508 is aligned with the center horizontal axis 760 and the second femur 512R is substantially perpendicular to the center horizontal axis 760, as indicated by the alignment indicators 168. No alignment instructions 166 are displayed upon the GUI 438 since the process 700 has determined that the second hip 510R is aligned.

In some implementations, the reporting service 660 stores the analyzed images 162a-c (and corresponding captured images 160a-c) within the non-transitory data store 170, each image 162a-c indicating a corresponding one of the pelvic center, non-operative hip 510L and operative hip 510R being aligned with the imaging device.

Referring to FIGS. 3, 4 and 8A-8D, the process 800 begins at block 802 after process 700 has been approved (e.g., block 744 of FIG. 7A) and fuses the previously analyzed images 162a-c of the pelvic center, the first hip 510L, and the second hip 510R determined to be aligned with the imaging device 16 to generate a fused image 164. The process 800 calculates a leg length measurement, a pelvic distance ($PD_R$), and a cup inclination angle of the second operative right hip 510R within the fused image 164 at block 806. In some examples, the process 800 further calculates, at block 806, a leg length measurement, a pelvic distance ($PD_L$), and a cup inclination angle of the first non-operative left hip 510L within the fused image 164. In some implementations, the process 800 further calculates, at block 806, an angle of major diameter of the cup (major cup angle diameter) based on the cup inclination angle 520R and the cup anteversion angle 522R.

The process 800 determines whether or not the leg length measurement of the second hip 510R is acceptable at block 810. In some examples, the leg length measurement is acceptable when the leg length measurement is within a predetermined leg length range (e.g., a predetermined range of acceptable leg length values). In other examples, the leg length is acceptable when a magnitude of a leg length difference between the first and second hips is less than a leg length difference threshold. If the process determines at block 810 that the leg length measurement is not acceptable, the second hip 510R is to be adjusted by the user 40 at block 816 and the process 700 is to be repeated to ensure proper alignment.

If the process determines at block 810 that the leg length measurement is acceptable, the process 800 determines, at block 812, whether or not the $PD_R$ is acceptable. In some examples, $PD_R$ is acceptable when the $PD_R$ is within a predetermined pelvic distance range (e.g., a predetermined range of acceptable pelvic distance values). In other examples, the $PD_R$ is acceptable when a magnitude of a femoral offset based on a difference between the pelvic distances $PD_R$, $PD_L$ is less than a femoral offset threshold (e.g., 3 mm). If the process 800 determines at block 812 that the $PD_R$ is not acceptable, the second hip 510R is to be adjusted by the user 40 at block 816 and the process 700 is to be repeated to ensure proper alignment.

If the process 800 determines at block 812 that the $PD_R$ is acceptable, the process 800 determines, at block 814, whether or not the cup inclination angle for the second hip 510R is acceptable. The cup inclination angle of the second hip 510R may be acceptable when the cup inclination angle is within a predetermined cup inclination angle range (e.g., 35 degrees to 45 degrees). If the process determines at block 814 that the cup inclination angle is not acceptable, the second hip 510R is to be adjusted by the user 40 at block 816 and the process 700 is to be repeated to ensure proper alignment. If the process 800 determines at block 814 that the cup inclination angle is not acceptable, the process 800 determines, at block 820, that the leg length, pelvic distance, and cup inclination angle measurements for the second hip 510R being operated upon for a replacement hip are approved. Accordingly, the reporting service 660 may store the fused image 164 within the non-transitory data store 176.

In some implementations, the process 800 determines, at block 814, whether or not the major cup diameter angle for the second hip 510R is acceptable in addition to, or in lieu of, the cup inclination angle determination. For instance, the major cup diameter angle of the second hip 510R may be acceptable when the major cup diameter angle is within a predetermined major cup diameter angle range (e.g., 35 degrees to 45 degrees). If the process determines at block 814 that the major cup diameter angle is not acceptable, the second hip 510R is to be adjusted by the user 40 at block 816 and the process 700 is to be repeated to ensure proper alignment. If the process 800 determines at block 814 that the major cup diameter angle is not acceptable, the process 800 determines, at block 820, that the leg length, pelvic distance, and major cup diameter angle measurements for the second hip 510R being operated upon for a replacement hip are approved. Accordingly, the reporting service 660 may store the fused image 165 within the non-transitory data store 176.

In some implementations, when any one of blocks 810, 812, or 814 indicate the associated hip parameter measurement is not acceptable, block 816 determines one or more implant instructions 890 for achieving acceptable leg length, pelvis distance, and major cup diameter angle measurements. The one or more implant instructions 890 (FIGS. 8B and 8C) may be transmitted to the user device 400 for display upon the GUI 436. For instance, alignment instructions may notify the surgeon 40 a proper cup size and/or stem size to be used for the replacement hip 51 OR such that all the hip parameter measurements will be acceptable.

Figure 8A:
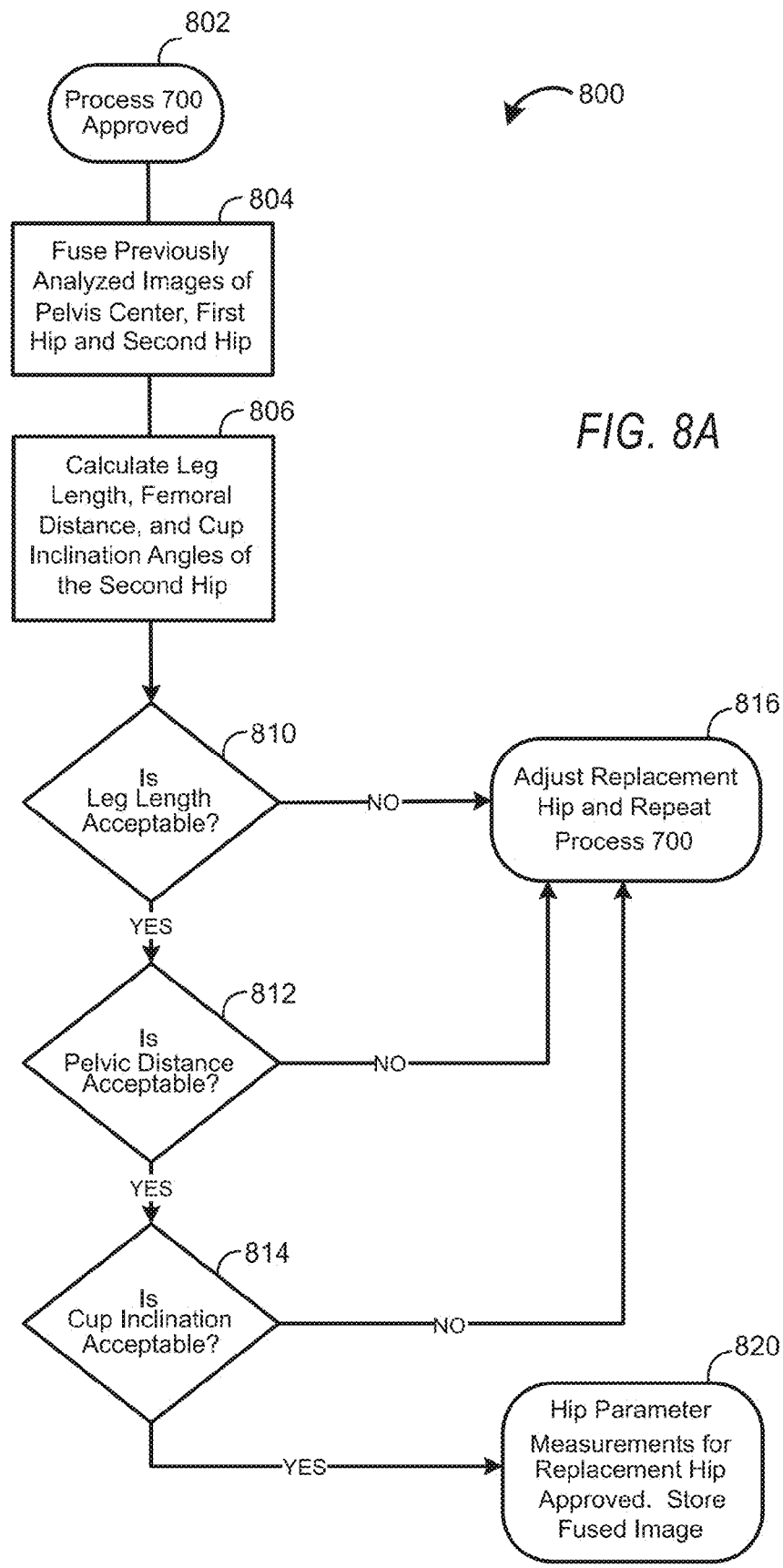
FIG. 8A shows an exemplary process for calculating a leg length measurement, a pelvic distance, and a cup inclination angle of a hip of a patient.
Figure 8B:
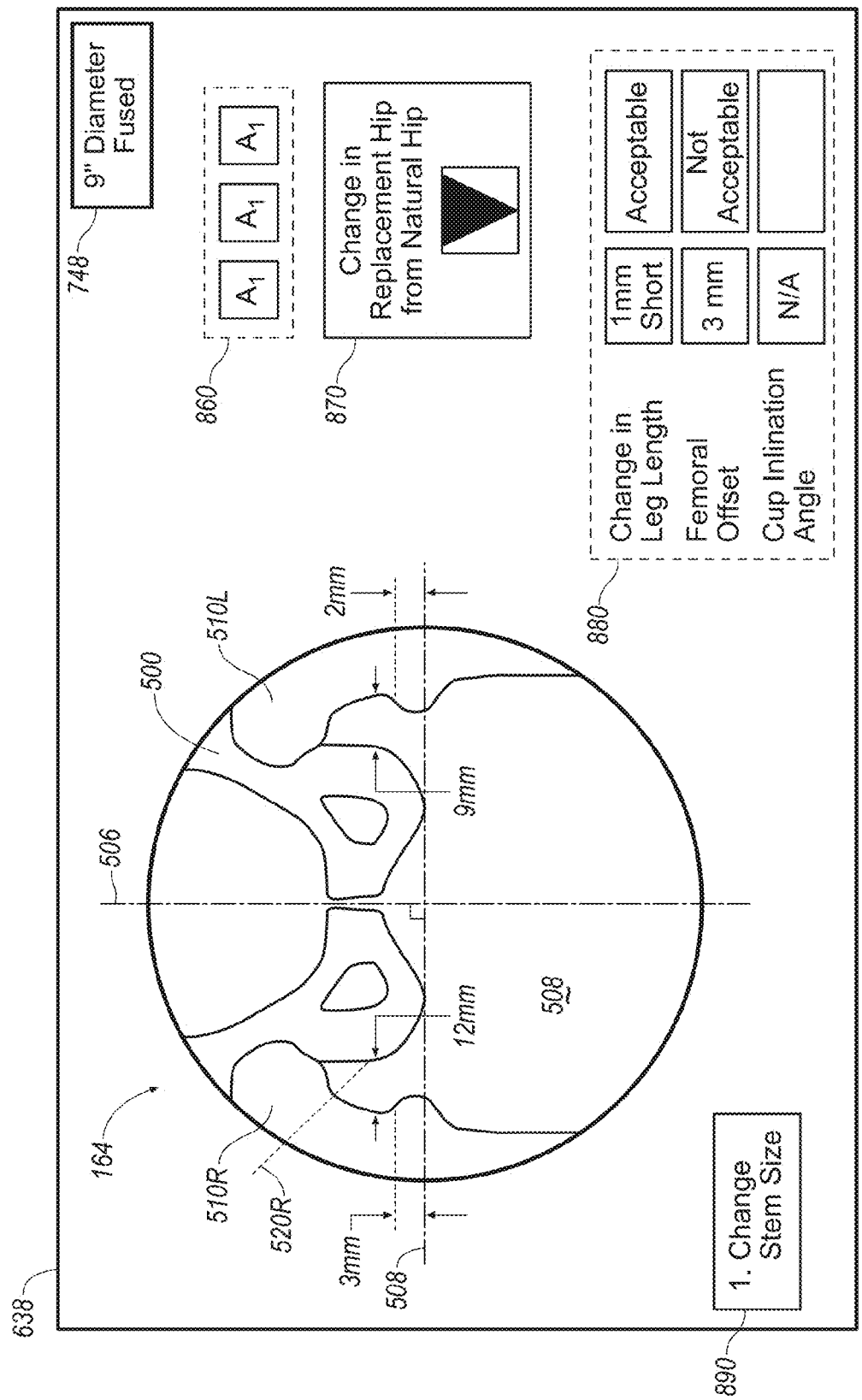
FIGS. 8B-8D show fused images of a pelvic area of a patient.
Figure 8C:
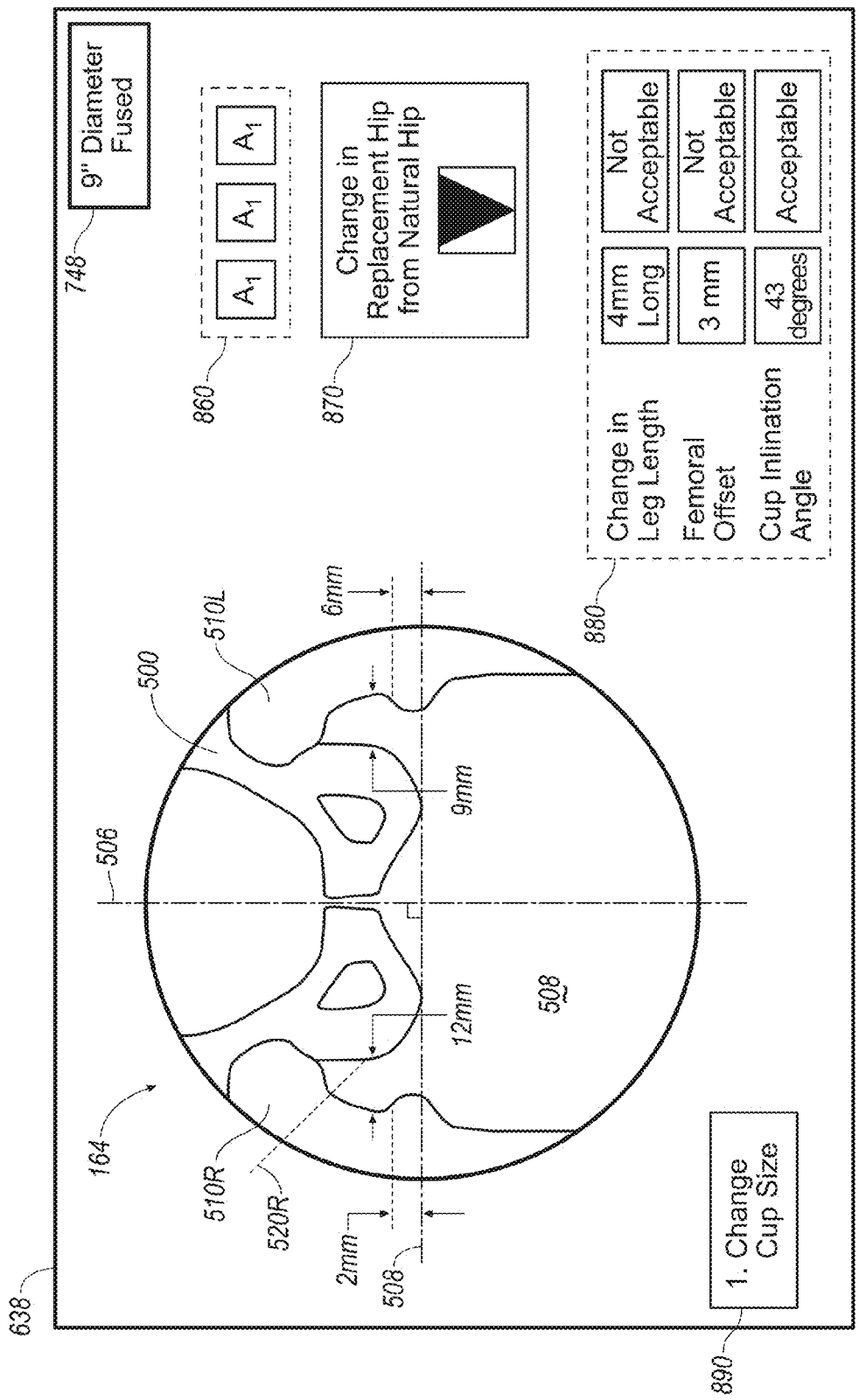
Figure 8D:
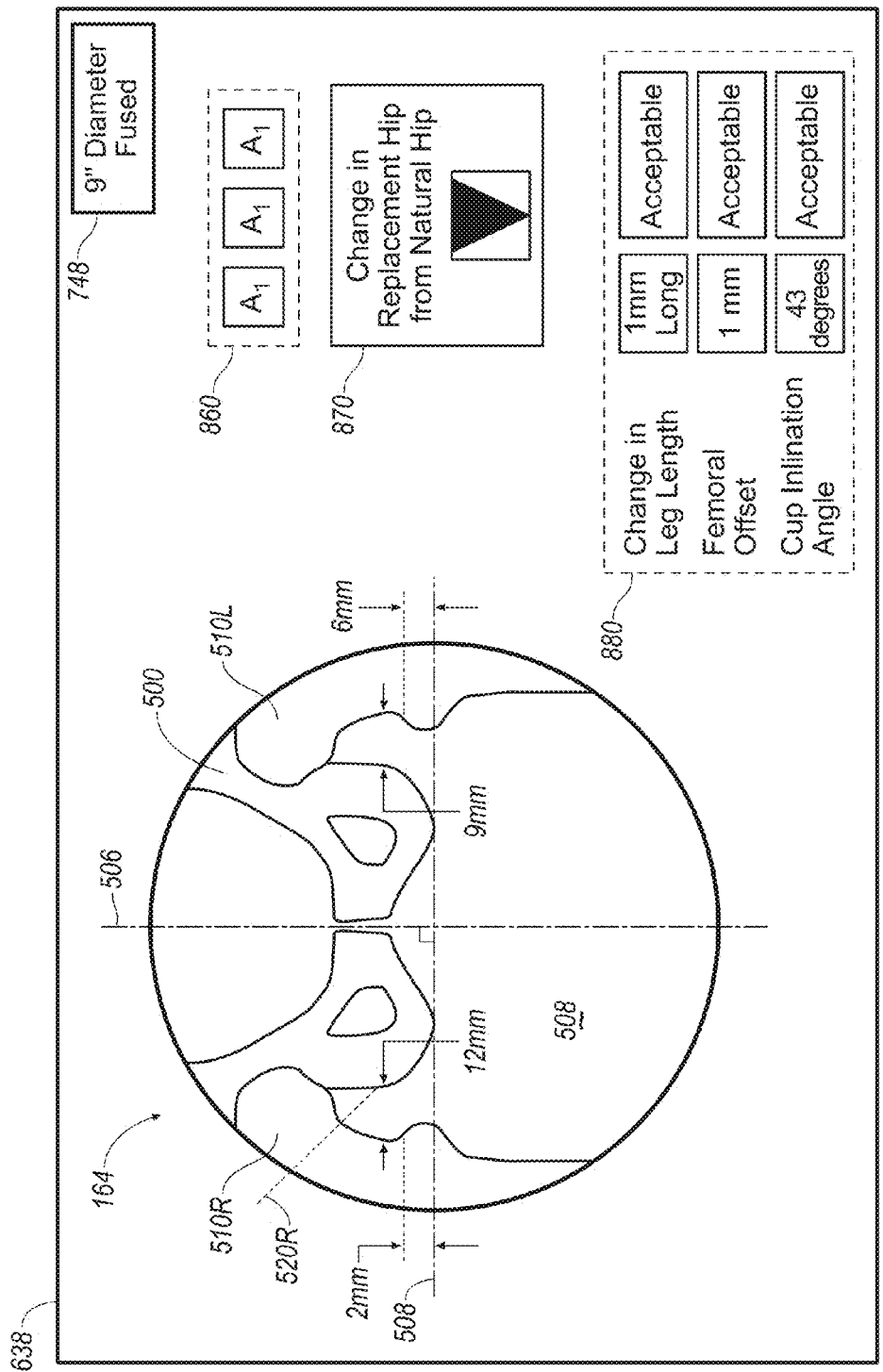

In some implementations, the hip parameter measurement service 640 transmits the fused image 160, the leg length measurement, the pelvic distance measurement, and the cup inclination angle measurement of the second hip 510R to the user device 400 for display upon the GUI 638. In some examples, the major cup diameter angle measurement may be transmitted instead of the cup inclination angle measurement of the second hip 510R. While the examples shown in FIGS. 8B-8D depict the cup inclination angle measurement, the major cup diameter measurement may be displayed and analyzed for acceptance. FIGS. 8B-8D show the fused image 164, imaging information 748, alignment information 860, hip calculation scheme 870 and calculated hip parameter measurement information 880. FIGS. 8B and 8C further show the one or more implant instructions 890 displayed upon the GUI 638. The alignment information 860 indicates that each of the pelvic center, first hip 510L and second hip 510R have been determined (via process 700) to be aligned with the imaging device 16. The hip calculation scheme 870 permits the user 40 to determine which hip parameter measurements will be analyzed. In the examples shown, changes between the measurements for the first and second hips 510L and 510R are being analyzed for comparison with corresponding predetermined threshold values. However, the user 40 may switch the scheme, and strictly analyze the hip parameter measurements of the second hip 510R for comparison with corresponding predetermined ranges of acceptable values.

Referring to FIG. 8B, the hip parameter measurement information 880 indicates to the user 40 that the magnitude of leg length difference between the first and second hips is equal to 1 mm long, and thus is acceptable. However, the magnitude of femoral offset is equal to 3 mm, and thus is not acceptable, since it is not less than the predetermined femoral offset threshold. Accordingly, process 800 will proceed to block 816 whereat the user 40 adjusts the second hip 510R and the pelvic area 18 must be re-aligned and verified at process 700 before new measurements are calculated. The implant instructions 890 may indicate one or more instructions to the surgeon 40 for achieving acceptable hip parameter measurements. For instance, the implant instructions 890 may indicate a new head size and/or stem size to use for the second hip 510R.

FIG. 8C includes new hip parameter measurement information 880 after the user 40 has adjusted the second hip 510R to correct the unacceptable femoral offset displayed in FIG. 8B. Now, the magnitude of leg length difference between the first and second hips is equal to 4 mm long, and thus is not acceptable, as it violates the predetermined leg length threshold. Likewise, the magnitude of femoral offset is still equal to 3 mm, and thus is not acceptable. Accordingly, process 800 will again proceed to block 816 whereat the user 40 adjusts the second hip 510R and the pelvic area 18 must be re-aligned and verified at process 700 before new measurements are calculated.

FIG. 8D includes new hip parameter measurement information 880 after the user 40 has adjusted the second hip 510R to correct the unacceptable leg length and femoral offset displayed in FIG. 8C. In the example shown, the hip parameter measurement information 880 indicates the leg length difference, the femoral offset, and the cup inclination angle are all acceptable (e.g., block 820 of FIG. 8A).

Figure 9:
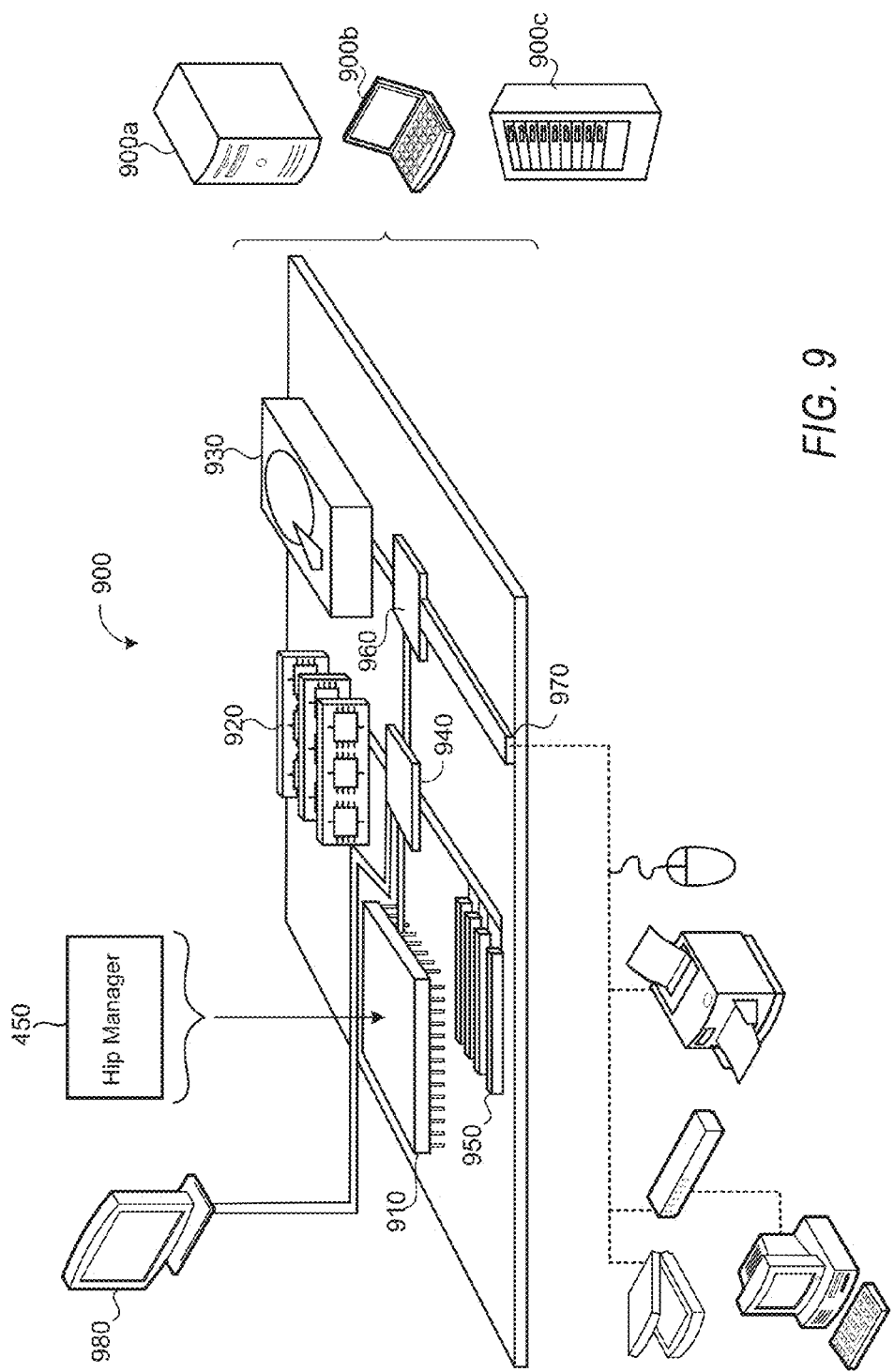
FIG. 9 is a schematic view of an example computing device executing the hip manager 450 of FIG. 3.

FIG. 9 is a schematic view of an example computing device 900 that may be used to implement the systems and methods described in this document, such as the hip manager 450 and the user device 400. The computing device 900 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 900 includes a processor 910 (i.e., processor), memory 920, a storage device 930, a high-speed interface/controller 940 connecting to the memory 920 and high-speed expansion ports 950, and a low speed interface/controller 960 connecting to a low speed bus 970 and storage device 930. Each of the components 910, 920, 930, 940, 950, and 960, are interconnected using various busses, and may be mounted on a common motherboard or in other manners as appropriate. The processor 910 can process instructions for execution within the computing device 900, including instructions stored in the memory 920 or on the storage device 930 to display graphical information for a GUI on an external input/output device, such as a display 980 coupled to a high speed interface 940. In other implementations, multiple processors and/or multiple buses may be used, as appropriate, along with multiple memories and types of memory. Also, multiple computing devices 900 may be connected, with each device providing portions of the necessary operations (e.g., as a server bank, a group of blade servers, or a multi-processor system).

The memory 920 stores information non-transitorily within the computing device 900. The non-transitory data store 170 may be within the memory 920. The memory 920 may be a computer-readable medium, a volatile memory unit(s), or non-volatile memory unit(s). The non-transitory memory 920 may be physical devices used to store programs (e.g., sequences of instructions) or data (e.g., program state information) on a temporary or permanent basis for use by the computing device 900. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 930 is capable of providing mass storage for the computing device 900. In some implementations, the storage device 930 is a computer-readable medium. In various different implementations, the storage device 930 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 920, the storage device 930, or memory on processor 910.

The high speed controller 940 manages bandwidth-intensive operations for the computing device 900, while the low speed controller 960 manages lower bandwidth-intensive operations. Such allocation of duties is exemplary only. In some implementations, the high-speed controller 940 is coupled to the memory 920, the display 980 (e.g., through a graphics processor or accelerator), and to the high-speed expansion ports 950, which may accept various expansion cards (not shown). In some implementations, the low-speed controller 960 is coupled to the storage device 930 and low-speed expansion port 970. The low-speed expansion port 970, which may include various communication ports (e.g., USB, Bluetooth, Ethernet, wireless Ethernet), may be coupled to one or more input/output devices, such as a keyboard, a pointing device, a scanner, or a networking device, such as a switch or router, e.g., through a network adapter.

The computing device 900 may be implemented in a number of different forms, as shown in the figure. For example, it may be implemented as a standard server 900a or multiple times in a group of such servers 900a, as a laptop computer 900b, or as part of a rack server system 900c.

Figure 10:
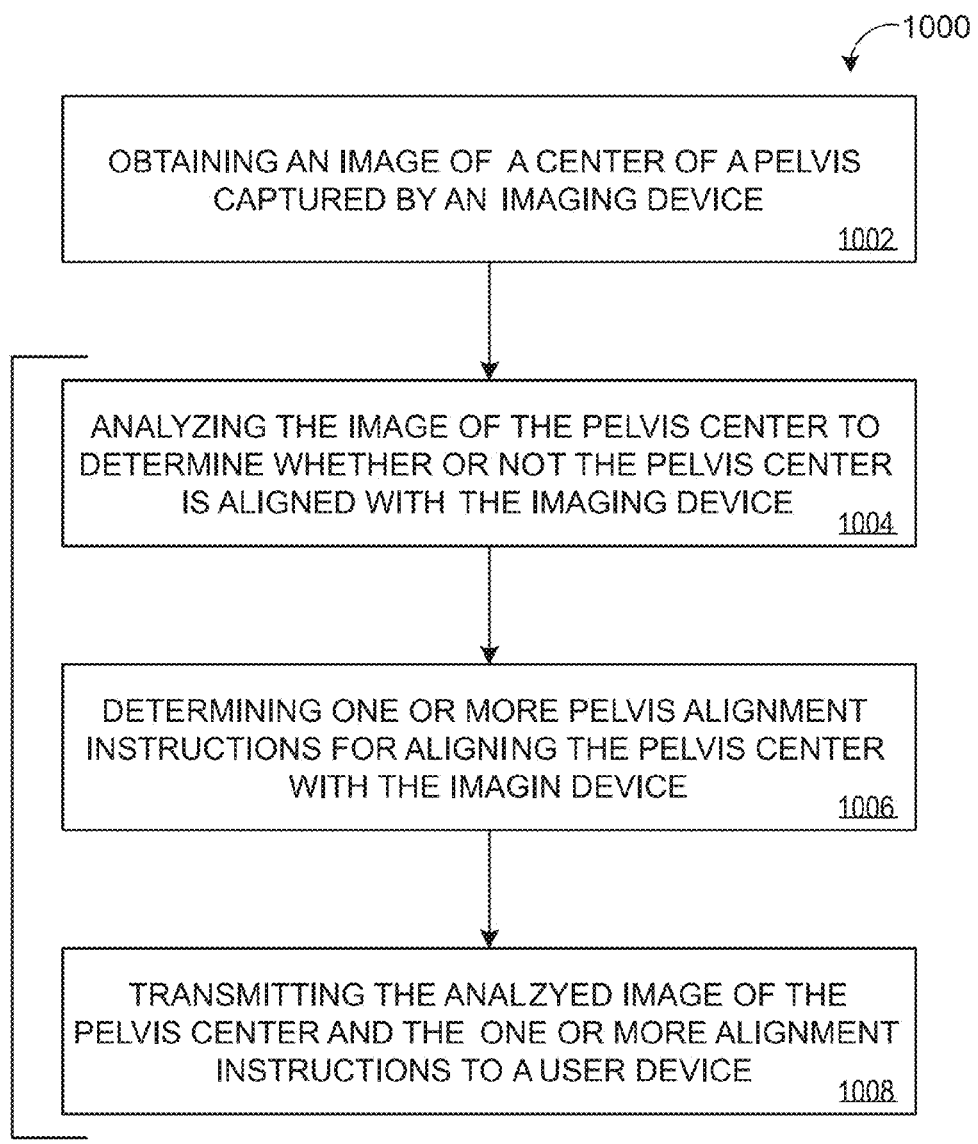
FIG. 10 is a flowchart of an example method for aligning a pelvic area of a patient with an imaging device.

FIG. 10 is a flowchart of an example method 1000 executed by the computing device 900 of FIG. 9 for aligning a pelvic area 18 of a patient 12 with an imaging device 16. The flowchart starts at operation 1002 where a hip manager 450 obtains an image 160 of a center of a pelvis of a patient captured by the imaging device 16, as shown at block 704 of process 700. Here, the imaging device 16 is positioned over the pelvis center to capture the image 160. In some examples, the captured image 160 is stored in the non-transitory data store 170 by the imaging device 16 and retrieved by the hip manager 450. In other examples, hip manager receives the captured image 160 from the imaging device 16. At operation 1004, the hip manager 450 analyzes the image 160 of the pelvis center to determine whether or not the pelvis center is aligned with the imaging device 16. For instance, the alignment service 656 of the hip manager 450 may identify anatomical landmarks, such as the transischial line 508 and the symphysis pubis line 506, within the captured image 160 and generate an analyzed image 162 including the identified anatomical landmarks, as shown at blocks 706 and 708 of process 700.

At operation 1006, when the hip manager 450 determines the pelvis center is not aligned with the imaging device 16, the hip manager 450 determines one or more pelvis alignment instructions 166 for aligning the pelvis center with the imaging device 16. For instance, block 714 of process 714 determines the one or more alignment instructions when block 712 determines the pelvis center is not aligned. At operation 1008, the hip manager 450 transmits the analyzed image 162 of the pelvis center and the one or more pelvis alignment instructions 166 to a user device 400 in communication with the hip manager 450. Additionally, at operation 1008, the hip manager 450 transmits the analyzed image 162 of the pelvis center and the one or more pelvis alignment instructions 166 to the imaging device 16 in communication with the hip manager 450 to cause the position of the imaging device 16 to change based on the alignment instructions 166. In some examples, the user device 400 executes a graphical user interface 438 for displaying the analyzed image 162 and one or more alignment instructions 166, as shown in FIG. 7C. The flowchart then reverts back to block 1002 to obtain a subsequent image of the pelvis center captured by the imaging device 16 after the user 40 has changed the orientation of the patient 12 and/or imaging device 16 based on the one or more alignment instructions 166. The flowchart iteratively executes operations 1002-1008 until the pelvis center is indicated as being aligned with the imaging device 16, as shown in FIG. 7D, as determined by block 712 of process 700.

Various implementations of the systems and techniques described here can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method comprising:
    obtaining, at a computing device in communication with an imaging device, an image of a center of a pelvis of a patient captured by the imaging device;
    analyzing, by the computing device, the image of the pelvis center to determine whether or not the pelvis center is aligned with the imaging device; and
    when the pelvis center is not aligned with the imaging device:
        determining, by the computing device, one or more pelvis alignment instructions for aligning the pelvis center with the imaging device; and
        transmitting the analyzed image of the pelvis center and the one or more pelvis alignment instructions to a user device in communication with the computing device, the user device executing a graphical user interface for displaying the analyzed image and the one or more pelvis alignment instructions.

2. The method of claim 1, further comprising, when analyzing the captured image of the pelvis center:
    identifying, by the computing device, a horizontal pelvis line and a symphysis pubis of the pelvis within the image of the pelvis center;
    determining, by the computing device, whether the horizontal pelvis line is aligned with a center horizontal axis of a field of view of the imaging device and whether the symphysis pubis is aligned with a center vertical axis of the field of view; and
    when at least one of the horizontal pelvis line or the symphysis pubis are not aligned, determining the pelvis center is not aligned with the imaging device.

3. The method of claim 1, further comprising, when analyzing the captured image of the pelvis center:
    identifying, by the computing device, first and second obturator foramens of the pelvis within the image of the pelvis center;
    determining, by the computing device, whether the first and second obturator foramens are substantially equal in at least one of size, shape, or symmetry with respect to a symphysis pubis of the pelvis; and
    when the first and second obturator foramens are not substantially equal in at least one of size, shape, or symmetry with respect to the symphysis pubis of the pelvis, determining the pelvis center is not aligned with the imaging device.

4. The method of claim 2, further comprising:
    registering, by the computing device, a transischial alignment graphic to the analyzed image of the pelvis center, the transischial alignment graphic comprising a first color when the horizontal pelvis line and the center horizontal axis are aligned and comprising a second color when the horizontal pelvis line and the center horizontal axis are not aligned;

registering, by the computing device, a symphysis pubis alignment graphic to the analyzed image of the pelvis center, the symphysis pubis graphic comprising the first color when the symphysis pubis and the center vertical axis are aligned and comprising the second color when the symphysis pubis and the center vertical axis are not aligned.

5. The method of claim 1, further comprising, when the pelvis center is aligned with the imaging device:
  obtaining, at the computing device, an image of a first hip of the patient captured by the imaging device;
  analyzing, by the computing device, the captured image of the first hip to determine whether or not the first hip is aligned with the imaging device; and
  when the first hip is not aligned with the imaging device:
    determining, by the computing device, one or more hip alignment instructions for aligning the first hip with the imaging device; and
    transmitting the analyzed image of the first hip and the one or more first hip alignment instructions to the user device for display upon the graphical user interface; and
  when the first hip is aligned with the imaging device:
    obtaining, at the computing device, an image of a second hip of the patient captured by the imaging device;
    analyzing, by the computing device, the captured image of the second hip to determine whether or not the second hip is aligned with the imaging device; and
    when the second hip is not aligned with the imaging device:
      determining, by the computing device, one or more second hip alignment instructions for aligning the second hip with the imaging device; and
      transmitting the analyzed image of the second hip and the one or more second hip alignment instructions to the user device for display upon the graphical user interface.

6. The method of claim 5, wherein the first hip is a non-operative hip and the second hip is a replacement hip.

7. The method of claim 5, further comprising:
  when analyzing the captured image of the first hip:
    identifying, by the computing device, a horizontal pelvis line and a first femur of the first hip within the image of the first hip;
    determining, by the computing device, whether the horizontal pelvis line is aligned with a center horizontal axis of a field of view of the imaging device and whether the first femur is substantially perpendicular to the center horizontal axis; and
    when at least one of the horizontal pelvis line is not aligned with the center horizontal axis or the first femur is not substantially perpendicular to the center horizontal axis, determining the first hip is not aligned with the imaging device.

8. The method of claim 7, further comprising:
  registering, by the computing device, a transischial alignment graphic to the analyzed image of the pelvis center, the transischial alignment graphic comprising a first color when the horizontal pelvis line and the center horizontal axis are aligned and comprising a second color when the horizontal pelvis line and the center horizontal axis are not aligned;
  registering, by the computing device, a vertical first femur alignment graphic to the analyzed image of the first hip, the vertical first femur alignment graphic comprising the first color when the first femur and the center horizontal axis are substantially perpendicular and comprising the second color when the first femur and the center horizontal axis are not substantially perpendicular.

9. The method of claim 5, further comprising:
  when analyzing the captured image of the second hip:
    identifying, by the computing device, a horizontal pelvis line and a second femur of the second hip within the image of the second hip;
    determining, by the computing device, whether the horizontal pelvis line is aligned with a center horizontal axis of a field of view of the imaging device and whether the second femur is substantially perpendicular to the center horizontal axis; and
    when at least one of the horizontal pelvis line is not aligned with the center horizontal axis or the second femur is not substantially perpendicular to the center horizontal axis, determining the second hip is not aligned with the imaging device.

10. The method of claim 9, further comprising:
  registering, by the computing device, a center horizontal axis alignment graphic to the analyzed image of the second hip, the center horizontal axis alignment graphic comprising a first color when the horizontal pelvis line and the center horizontal axis are aligned and comprising a second color when the horizontal pelvis line and the center horizontal axis are not aligned; and
  registering, by the computing device, a second femur alignment graphic to the analyzed image of the second hip, the second femur alignment graphic comprising the first color when the second femur and the center horizontal axis are substantially perpendicular and comprising the second color when the first femur and the center horizontal axis are not substantially perpendicular.

11. The method of claim 5, further comprising transmitting one of the pelvis center, the first hip, or the second hip alignment instructions to the imaging device, the imaging device comprising:
  at least one motor for adjusting a position of the imaging device; and
  a motor controller in communication with the motor, the motor controller, when executing the one of the pelvis center, the first hip, or the second hip alignment instructions, causing the motor to adjust the position of the imaging device based on the one of the pelvis center, the first hip, or the second hip alignment instructions.

12. The method claim 5, further comprising, when the computing device determines images captured by the imaging device of the pelvis center, a first hip, and a second hip are all aligned with the imaging device:
  fusing, by the computing device, the previously analyzed images of the pelvis center, the first hip, and the second hip to generate a fused image;
  calculating, by the computing device, a leg length measurement, a pelvic distance measurement, and a major cup diameter angle of the second hip within the fused image;

determining, by the computing device, whether or not the leg length measurement, the pelvic distance measurement, and the major cup diameter angle of the second hip are acceptable;

transmitting the fused image, the a leg length measurement, the pelvic distance measurement, and the major cup diameter angle of the second hip to the user device for display upon the graphical user interface.

13. The method of claim 12, further comprising when determining whether or not the leg length measurement, the pelvic distance measurement, and the major cup diameter angle of the second hip are acceptable:

determining the leg length measurement of the second hip is acceptable when the leg length measurement is within a predetermined leg length range;

determining the pelvic distance measurement of the second hip is acceptable when the pelvic distance measurement is within a predetermined pelvic distance range; and determining the major cup diameter angle of the second hip is acceptable when the major cup diameter angle is within a predetermined major cup diameter angle range.

14. The method of claim 12, further comprising when determining whether or not the leg length measurement, the pelvic distance measurement, and the major cup diameter angle of the second hip are acceptable:

calculating, by the computing device, a leg length measurement and a pelvic distance measurement of the first hip within the fused image;

determining the leg length measurement of the second hip is acceptable when a magnitude of a leg length difference between the first and second hips is less than a leg length difference threshold;

determining the pelvic distance measurement of the second hip is acceptable when a magnitude of a femoral offset based on a difference between the pelvic distances of the first and second hips is less than a femoral offset threshold; and determining the major cup diameter angle of the second hip is acceptable when the major cup diameter angle is within a predetermined major cup diameter angle range.

15. The method of claim 12, further comprising:

when at least one of the a leg length measurement, the pelvic distance measurement, and the major cup diameter angle of the second hip are not acceptable, determining, by the computing device, one or more implant instructions for achieving acceptable leg length, pelvic distance, and major cup diameter angle measurements;

transmitting the one or more implant instructions from the computing device to the user device; and storing the fused image within a non-transitory data store in communication with the computing device.

16. A system comprising:

an imaging device; and one or more alignment processing devices in communication with the imaging device and executing an alignment service, the alignment service encoded on a non-transitory computer readable storage medium and comprising instructions that, when executed by the one or more alignment processing devices, cause the one or more alignment processing devices to perform operations comprising:

obtaining an image of a center of a pelvis of a patient captured by the imaging device;

analyzing the image of the pelvis center to determine whether or not the pelvis center is aligned with the imaging device; and when the pelvis center is not aligned with the imaging device:

determining one or more pelvis alignment instructions for aligning the pelvis center with the imaging device; and transmitting the analyzed image of the pelvis center and the one or more pelvis alignment instructions to a user device in communication with the alignment service, the user device executing a graphical user interface for displaying the analyzed image and the one or more pelvis alignment instructions.

17. The system of claim 16, wherein the alignment service, at the one or more alignment processing devices, when analyzing the captured image of the pelvis center, further comprises instructions that, when executed by the one or more alignment processing devices, cause the one or more alignment processing devices to perform operations comprising:

identifying a horizontal pelvis line and a symphysis pubis of the pelvis within the image of the pelvis center;

determining whether the horizontal pelvis line is aligned with a center horizontal axis of a field of view of the imaging device and whether the symphysis pubis is aligned with a center vertical axis of the field of view; and when at least one of the horizontal pelvis line or the symphysis pubis are not aligned, determining the pelvis center is not aligned with the imaging device.

18. The system of claim 16, wherein the alignment service, at the one or more alignment processing devices, when analyzing the captured image of the pelvis center, further comprises instructions that, when executed by the one or more alignment processing devices, cause the one or more alignment processing devices to perform operations comprising:

identifying first and second obturator foramens of the pelvis within the image of the pelvis center;

determining whether the first and second obturator foramens are substantially equal in at least one of size, shape, or symmetry with respect to a symphysis pubis of the pelvis; and when the first and second obturator foramens are not substantially equal in at least one of size, shape, or symmetry with respect to a symphysis pubis of the pelvis, determining the pelvis center is not aligned with the imaging device.

19. The system of claim 17, wherein the alignment service, at the one or more alignment processing device, further comprises instructions that, when executed by the one or more alignment processing devices, cause the one or more alignment processing devices to perform operations comprising:

registering a transischial alignment graphic to the analyzed image of the pelvis center, the transischial alignment graphic comprising a first color when the horizontal pelvis line and the center horizontal axis are aligned and comprising a second color when the horizontal pelvis line and the center horizontal axis are not aligned;

registering a symphysis pubis alignment graphic to the analyzed image of the pelvis center, the symphysis pubis graphic comprising the first color when the symphysis pubis and the center vertical axis are aligned and comprising the second color when the symphysis pubis and the center vertical axis are not aligned.

20. The system of claim 16, wherein the alignment service, at the one or more alignment processing devices, further comprises instructions that, when executed by the one or more alignment processing devices, cause the one or more alignment processing devices to perform operations comprising:
obtaining an image of a first hip of the patient captured by the imaging device;
analyzing the captured image of the first hip to determine whether or not the first hip is aligned with the imaging device; and
when the first hip is not aligned with the imaging device:
determining one or more hip alignment instructions for aligning the first hip with the imaging device; and
transmitting the analyzed image of the first hip and the one or more hip alignment instructions to the user device for display upon the graphical user interface; and
when the first hip is aligned with the imaging device:
obtaining an image of a second hip of the patient captured by the imaging device;
analyzing the captured image of the second hip to determine whether or not the second hip is aligned with the imaging device; and
when the second hip is not aligned with the imaging device:
determining one or more second hip alignment instructions for aligning the second hip with the imaging device; and
transmitting the analyzed image of the second hip and the one or more second hip alignment instructions to the user device for display upon the graphical user interface.

21. The system of claim 20, wherein the first hip is a non-operative hip and the second hip is a replacement hip.

22. The system of claim 20, wherein the alignment service, at the one or more alignment processing devices, when analyzing the captured image of the first hip, further comprises instructions that, when executed by the one or more alignment processing devices, cause the one or more alignment processing devices to preform operations comprising:
identifying a horizontal pelvis line and a first femur of the first hip within the image of the first hip;
determining whether the horizontal pelvis line is aligned with a center horizontal axis of a field of view of the imaging device and whether the first femur is substantially perpendicular to the center horizontal axis; and
when at least one of the horizontal pelvis line is not aligned with the center horizontal axis or the first femur is not substantially perpendicular to the center horizontal axis, determining the first hip is not aligned with the imaging device.

23. The system of claim 22, wherein the alignment service, at the one or more alignment processing devices, further comprises instructions that, when executed by the one or more alignment processing devices, cause the one or more alignment processing devices to perform operations comprises:
registering a transischial alignment graphic to the analyzed image of the pelvis center, the transischial alignment graphic comprising a first color when the horizontal pelvis line and the center horizontal axis are aligned and comprising a second color when the horizontal pelvis line and the center horizontal axis are not aligned;
registering a vertical first femur alignment graphic to the analyzed image of the first hip, the vertical first femur alignment graphic comprising the first color when the first femur and the center horizontal axis are substantially perpendicular and comprising the second color when the first femur and the center horizontal axis are not substantially perpendicular.

24. The system of claim 22, wherein the alignment service, at the one or more alignment processing devices, when analyzing the captured image of the second hip, further comprises instructions that, when executed by the one or more alignment processing devices, cause the one or more alignment processing devices to perform operations comprising:
identifying a horizontal pelvis line and a second femur of the second hip within the image of the second hip;
determining whether the horizontal pelvis line is aligned with a center horizontal axis of a field of view of the imaging device and whether the second femur is substantially perpendicular to the center horizontal axis; and
when at least one of the horizontal pelvis line is not aligned with the center horizontal axis or the second femur is not substantially perpendicular to the center horizontal axis, determining the second hip is not aligned with the imaging device.

25. The system of claim 24, wherein the alignment service, at the one or more alignment processing devices:
registering a center horizontal axis alignment graphic to the analyzed image of the second hip, the center horizontal axis alignment graphic comprising a first color when the horizontal pelvis line and the center horizontal axis are aligned and comprising a second color when the horizontal pelvis line and the center horizontal axis are not aligned; and
a registering a second femur alignment graphic to the analyzed image of the second hip, the second femur alignment graphic comprising the first color when the second femur and the center horizontal axis are substantially perpendicular and comprising the second color when the first femur and the center horizontal axis are not substantially perpendicular.

26. The system of claim 20, wherein the alignment service, at the one or more alignment processing devices, further comprises instructions that, executed by the one or more alignment processing devices, cause the one or more alignment processing devices to perform operations comprising transmitting one of the one or more pelvis alignment instructions, the one or more hip alignment instructions, or the one or more second hip alignment instructions to the imaging device, the imaging device comprising:
at least one motor for adjusting a position of the imaging device; and
a motor controller in communication with the motor, the motor controller, when executing the one of the one or more pelvis alignment instructions, the hip alignment instructions, or the second hip alignment instructions, configured to cause the motor to adjust the position of the imaging device based on the one of the one or more pelvis alignment instructions, the hip alignment instructions, or the second hip alignment instructions.

27. The system of claim 16, further comprising one or more hip parameter measurement processing devices in communication with the alignment service and executing a hip parameter measurement service, the hip parameter measurement service encoded on the non-transitory computer readable storage medium and comprising instructions that, when executed by the one or more hip parameter measurement processing devices, cause the one or more hip parameter measurement processing devices to perform operations comprising:

when the alignment service determines images captured by the imaging device of the pelvis center, a first hip, and a second hip are all aligned with the imaging device:
fusing the previously analyzed images of the pelvis center, the first hip, and the second hip to generate a fused image;
calculating leg length measurement, a pelvic distance measurement, and a cup inclination angle of the second hip within the fused image;
determining whether or not the leg length measurement, the pelvic distance measurement, and the cup inclination angle of the second hip are acceptable;
transmitting the fused image, the a leg length measurement, the pelvic distance measurement, and the cup inclination angle of the second hip to the user device for display upon the graphical user interface.

28. The system of claim 27, wherein the hip parameter measurement service, at the one or more hip parameter measurement processing devices, when determining whether or not the leg length measurement, the pelvic distance measurement, and the cup inclination angle of the second hip are acceptable, further comprises instructions that, when executed by the one or more hip are parameter measurement processing devices, cause the one or more hip parameter measurement processing devices to perform operations comprising:

determining the leg length measurement of the second hip is acceptable when the leg length measurement is within a predetermined leg length range;
determining the pelvic distance measurement of the second hip is acceptable when the pelvic distance measurement is within a predetermined pelvic distance range; and
determining the cup inclination angle of the second hip is acceptable when the cup inclination angle is within a predetermined cup inclination angle range.

29. The system of claim 27, wherein the hip parameter measurement service, at the one or more hip parameter measurement processing devices, when determining whether or not the leg length measurement, the pelvic distance measurement, and the cup inclination angle of the second hip are acceptable, further comprises instructions that, when executed by the one or more hip parameter measurement processing devices, cause the one or more hip parameter measurement processing devices to perform operations comprising:

calculating a leg length measurement and a pelvic distance measurement of the first hip within the fused image;
determining the leg length measurement of the second hip is acceptable when a magnitude of a leg length difference between the first and second hips is less than a leg length difference threshold;
determining the pelvic distance measurement of the second hip is acceptable when a magnitude of a femoral offset based on a difference between the pelvic distances of the first and second hips is less than a femoral offset threshold; and
determining a the cup inclination angle of the second hip is acceptable when the cup inclination angle is within a predetermined cup inclination angle range.

30. The system of claim 27, further comprising one or more reporting processing devices in communication with the hip parameter measurement service and executing a reporting service, the reporting service encoded on the non-transitory computer readable storage medium and comprising instructions that, when executed by the one or more reporting processing devices, cause the one or more reporting processing devices to perform operation comprising:

storing the fused image within a non-transitory data store in communication with the reporting service; and
wherein the hip parameter measurement service, at the one or more hip parameter measurement processing devices, further comprises instructions that, when executed by the one or more hip parameter measurement processing devices, cause the one or more hip parameter measurement processing devices to perform operation comprising:
when at least one of the a leg length measurement, the pelvic distance measurement, and the cup inclination angle of the second hip are not acceptable,
determining one or more implant instructions for achieving acceptable leg length, pelvic distance, and cup inclination angle measurements; and
transmitting the one or more implant instructions to the user device.

* * * * *